US012147601B1

(12) United States Patent
Laufer et al.

(10) Patent No.: US 12,147,601 B1
(45) Date of Patent: Nov. 19, 2024

(54) REMOVING EYE BLINKS FROM EMG SPEECH SIGNALS

(71) Applicant: Snap Inc., Santa Monica, CA (US)

(72) Inventors: Yaron Laufer, Brookline, MA (US); Assif Ziv, Beit Yitzhak-Sha'ar Hefer (IL)

(73) Assignee: Snap Inc., Santa Monica, CA (US)

( * ) Notice: Subject to any disclaimer, the term of this patent is extended or adjusted under 35 U.S.C. 154(b) by 0 days.

(21) Appl. No.: 17/661,203

(22) Filed: Apr. 28, 2022

(51) Int. Cl.
*G06F 3/01* (2006.01)
*A61B 5/00* (2006.01)
*A61B 5/394* (2021.01)

(52) U.S. Cl.
CPC .............. *G06F 3/015* (2013.01); *A61B 5/394* (2021.01); *A61B 5/721* (2013.01); *A61B 5/7246* (2013.01); *A61B 5/7253* (2013.01); *A61B 5/7267* (2013.01)

(58) Field of Classification Search
CPC ......... G06F 3/015; A61B 5/394; A61B 5/721; A61B 5/7246; A61B 5/7253; A61B 5/7267
See application file for complete search history.

(56) References Cited

U.S. PATENT DOCUMENTS

| 6,625,485 | B2 | 9/2003 | Levendowski et al. |
| 7,499,894 | B2 | 3/2009 | Marom et al. |
| 7,606,623 | B2 | 10/2009 | Ludlow et al. |
| 11,413,425 | B2 | 8/2022 | Poltorak |
| 11,504,038 | B2 | 11/2022 | Howard |
| 11,607,547 | B2 | 3/2023 | Osorio |
| 11,786,694 | B2 | 10/2023 | Poltorak |
| 2005/0240253 | A1 | 10/2005 | Tyler et al. |
| 2006/0241718 | A1 | 10/2006 | Tyler et al. |

(Continued)

FOREIGN PATENT DOCUMENTS

| CN | 104023790 A | 9/2014 |
| CN | 107427675 A | 12/2017 |

(Continued)

OTHER PUBLICATIONS

Kapur, Arnav, "AlterEgo A Personalized Wearable Silent Speech Interface", IUI 2018 Session 1B Multimodal Interfaces, (Mar. 7, 2018), 10 pgs.

*Primary Examiner* — Robert J Michaud
(74) *Attorney, Agent, or Firm* — Schwegman Lundberg & Woessner, P.A.

(57) ABSTRACT

Systems and methods are provided for performing operations comprising: detecting, by a plurality of electromyograph (EMG) electrodes of an EMG communication device, subthreshold muscle activation signals of one or more muscles associated with speech production, the subthreshold muscle activation signals being generated in response to inner speech of a user; applying a transform to the subthreshold muscle activation signals detected by the plurality of EMG electrodes to represent the subthreshold muscle activation signals as a plurality of maximally independent components; accessing an interference template corresponding to an eye blink component; filtering the plurality of maximally independent components based on the interference template to provide filtered maximally independent components; and regenerating a filtered version of the subthreshold muscle activation signals based on the filtered maximally independent components.

20 Claims, 14 Drawing Sheets

(56) References Cited

U.S. PATENT DOCUMENTS

| | | | |
|---|---|---|---|
| 2008/0009772 | A1 | 1/2008 | Tyler et al. |
| 2009/0062680 | A1 | 3/2009 | Sandford |
| 2009/0264786 | A1* | 10/2009 | Jacquin ................. A61B 5/369 |
| | | | 708/323 |
| 2017/0258390 | A1 | 9/2017 | Howard |
| 2019/0295566 | A1* | 9/2019 | Moghadamfalahi ... A61B 5/318 |
| 2020/0060566 | A1 | 2/2020 | Howard |
| 2022/0111207 | A1 | 4/2022 | Osorio |
| 2022/0296155 | A1 | 9/2022 | Osorio |
| 2022/0387749 | A1 | 12/2022 | Poltorak |

FOREIGN PATENT DOCUMENTS

| | | |
|---|---|---|
| CN | 107427685 A | 12/2017 |
| CN | 113382683 A | 9/2021 |
| CN | 110167630 B | 12/2023 |
| EP | 0971628 B1 | 4/2005 |
| EP | 1795122 A1 | 6/2007 |
| JP | 2007504165 A | 3/2007 |
| JP | 5956618 B2 | 6/2016 |
| JP | 6184989 B2 | 8/2017 |
| TW | 200845959 A | 12/2008 |
| WO | WO-2016033609 A1 | 3/2016 |
| WO | WO-2019133997 A1 | 7/2019 |
| WO | WO-2020081609 A1 | 4/2020 |
| WO | WO-2021026400 A1 | 2/2021 |

* cited by examiner

REMOVING EYE BLINKS FROM EMG SPEECH SIGNALS

FIELD OF USE

This disclosure relates to electromyograph (EMG) speech systems and to messaging applications or AR/VR devices.

BACKGROUND

Some electronics-enabled devices include various input interfaces to allow a user to communicate with other users. Such input interfaces include voice message interfaces that enable users to send verbal messages to others. Other input interfaces include textual input in which a user types in their desired message. These types of input interfaces require movement by users, such as moving facial muscles to produce speech for verbal messages or moving fingers to select different keys on a keyboard.

BRIEF DESCRIPTION OF THE DRAWINGS

Various ones of the appended drawings merely illustrate examples of the present disclosure and should not be considered as limiting its scope.

DETAILED DESCRIPTION

Figure 1:
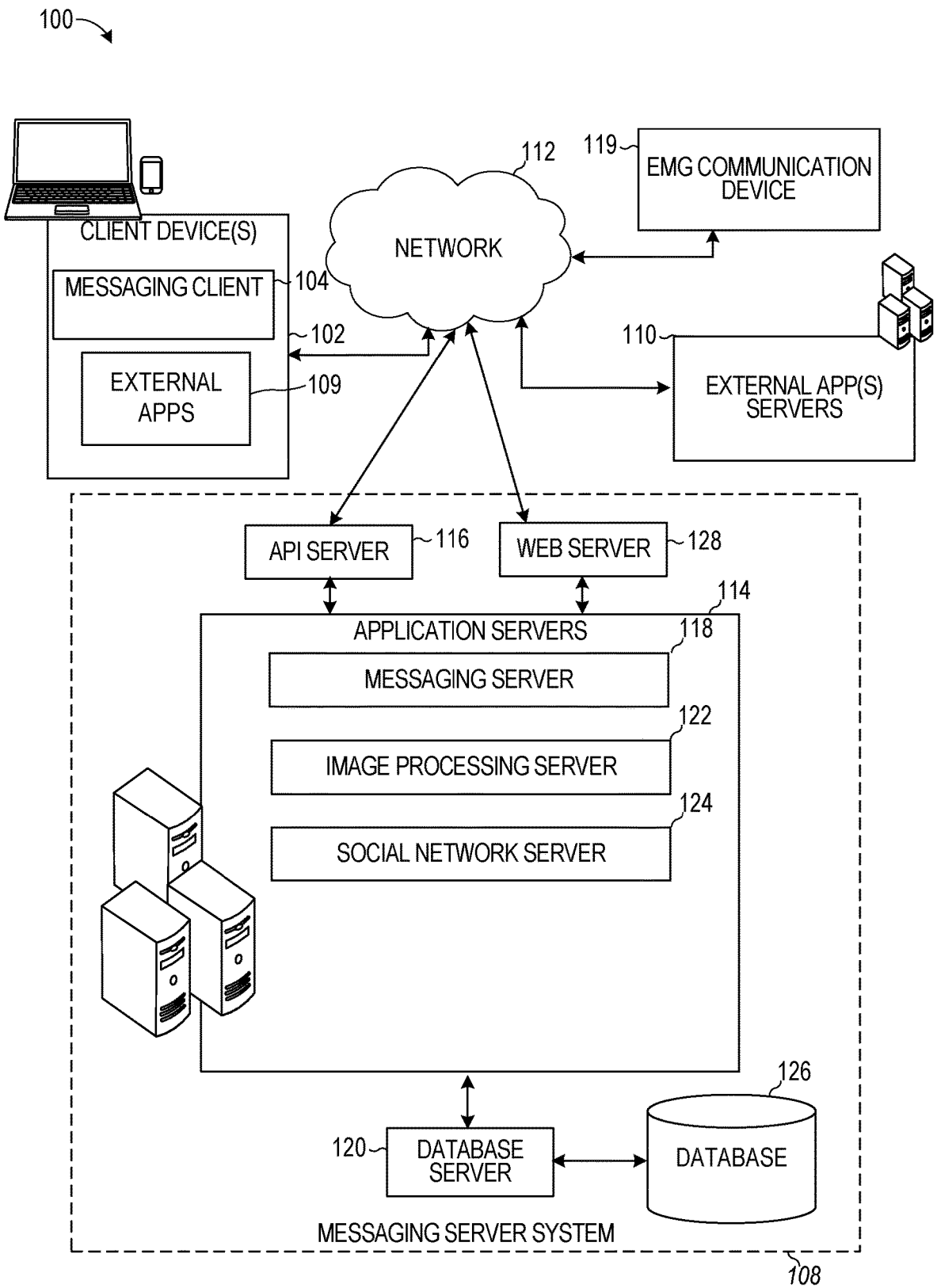
FIG. 1 is a diagrammatic representation of a networked environment in which the present disclosure may be deployed, in accordance with some examples.

The description that follows discusses illustrative examples of the disclosure. In the following description, for the purposes of explanation, numerous specific details are set forth in order to provide an understanding of various examples of the disclosed subject matter. It will be evident, however, to those skilled in the art, that examples of the disclosed subject matter may be practiced without these specific details. In general, well-known instruction instances, protocols, structures, and techniques are not necessarily shown in detail.

Typical non-invasive brain computer interfaces use electroencephalography (EEG) sensors. Such systems detect neural signals in a brain of a user and decode the neural signals into various operations. These systems can consume a great deal of energy and can be difficult to place on a user's head accurately. Other non-invasive computer interfaces leverage electromyograph (EMG) electrodes, which detect muscle activity. Such systems rely on surface measurement of muscle signals (represented by EMG signals) to discriminate and recognize sub-audible speech signals produced with relatively little or no acoustic input. The EMG signals can be measured on the side of a subject's throat, near the larynx.

Specifically, when a person intends to speak a word or phrase, the person's brain generates a neural signal and provides that neural signal to the corresponding speech-producing muscles, such as the larynx, throat, tongue, and so forth. Subthreshold muscle activation is a phenomenon that occurs when a person performs inner speech by imagining a motor activity or giving attention to another human movement while focusing on specific words or phrases. In such cases, the brain's motor cortex (M1) sends a neural signal to the relevant muscles. The signal is too subtle to fully activate the muscle. However, the signal can be detected by EMG electrodes. Because such a signal is about 10× clearer than the corresponding neural signals that can be detected by EEG, improved decoding of intended operations can be performed. Speaking is a motor activity, but thinking about speech is not a motor activity. Inner speech refers to the voluntary act of saying something silently (e.g., vividly imagining speaking), without moving the tongue and facial muscles, strictly to oneself.

Users are always seeking new ways to communicate with others and to control their devices. Typical systems enable such communications by performing overt actions, which in some cases cannot be performed. For example, if a user is composing a verbal message in a public environment, the user's speech can be heard by others which invades the user's privacy. Such a user may avoid composing the message until a later time which can be burdensome. Also, many speech-to-text systems that operate using the voice of the user are still inaccurate and erroneously generate messages based on a user's speech. The users in such systems still need to manually perform corrections which results in inefficient use of resources or lack of use.

Certain systems use EMG electrodes to detect inner speech of users. The inner speech can then be used in these systems to perform various operations. The success of these systems in detecting the inner speech heavily relies upon the accuracy of the EMG signals collected by the EMG electrodes. Namely, the system can accurately detect inner speech when the EMG signals are not prone to external interference. In many cases, users often perform involuntary gestures, such as blinking their eyes, while they talk or even while they perform inner speech. Such involuntary gestures can be represented by the EMG signals collected by the EMG electrodes. This creates noise and interference in the EMG signals which reduces the accuracy at which the inner speech can be detected from the EMG signals.

The disclosed examples improve the efficiency of using the electronic device by providing a system that removes artifacts or noise from EMG signals to enable a user to communicate and interact with a mobile device using the EMG signals. Specifically, the disclosed examples can detect, by a plurality of EMG electrodes of an EMG communication device, subthreshold muscle activation signals of one or more muscles associated with speech production. The subthreshold muscle activation signals can be generated in response to inner speech of a user. The disclosed examples apply a transform to the subthreshold muscle activation signals detected by the plurality of EMG electrodes to represent the subthreshold muscle activation signals as a plurality of maximally independent components. The disclosed examples access an interference template corresponding to an eye blink component and filter the plurality of maximally independent components based on the interference template to provide filtered maximally independent components. The disclosed examples regenerate a filtered version of the subthreshold muscle activation signals based on the filtered maximally independent components. A visual or audible output is generated based on the filtered version of the subthreshold muscle activation signals and the visual or audible output is caused to be processed by a messaging application to engage a feature of the messaging application.

In some examples, the disclosed examples include an EMG communication device that includes a wearable collar, earphones, communication device, and a processing device. The EMG communication device can be in communication with a mobile device, an AR headset, a VR headset, and/or with headphones, earbuds, or speakers. The disclosed techniques employ a technique to analyze EMG and/or sound signals, filter out interfering components (e.g., involuntary gestures, such as eye blinks) from the EMG signals, and synthesize, from the filtered EMG signals, filtered voice that corresponds to the inner speech, and/or to output the words as text on a digital medium, such as a chat message that is part of a communication session.

This allows the user to interact with features of a messaging application without performing any overt physical movement. Namely, a user can compose a message by performing inner speech and without moving any muscles associated with speech production or typing. This reduces the number of resources needed to operate a given device and improves the overall efficiency of electronic devices. This increases the efficiency, appeal, and utility of electronic devices. The disclosed examples increase the efficiencies of the electronic device by reducing the number of pages of information and inputs needed to accomplish a task.

Networked Computing Environment

FIG. 1 is a diagrammatic representation of a networked environment of a messaging system 100 in which the present disclosure may be deployed, in accordance with some examples. The messaging system 100 includes multiple instances of a client device 102, each of which hosts a number of applications, including a messaging client 104 and other external applications 109 (e.g., third-party applications). Each messaging client 104 is communicatively coupled to other instances of the messaging client 104 (e.g., hosted on respective other client devices 102), a messaging server system 108 and external app(s) servers 110 via a network 112 (e.g., the Internet). A messaging client 104 can also communicate with locally-hosted third-party applications 109 using Application Program Interfaces (APIs).

The messaging system 100 can include an EMG communication device 119, which can host an EMG speech detection system 222 (FIG. 2), among other applications. The EMG communication device 119 is communicatively coupled to the client device 102 via the network 112 (which may include via a dedicated short-range communication path, such as a Bluetooth™ or WiFi direct connection, and can also include a long-range communication path, such as the Internet). The EMG communication device 119 can include similar functionality as the client devices 102. In some cases, the client devices 102 also or alternatively implement an instance of the EMG speech detection system 222.

The client device 102 may operate as a standalone device or may be coupled (e.g., networked) to other machines. In a networked deployment, the client device 102 may operate in the capacity of a server machine or a client machine in a server-client network environment, or as a peer machine in a peer-to-peer (or distributed) network environment. The client device 102 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smartphone, a mobile device, a wearable device (e.g., a smartwatch), a smart home device (e.g., a smart appliance), other smart devices, a web appliance, a network router, a network switch, a network bridge, or any machine capable of executing the disclosed operations. Further, while only a single client device 102 is illustrated, the term "client device" shall also be taken to include a collection of machines that individually or jointly execute the disclosed operations.

In some examples, the client device 102 can include AR glasses or an AR headset in which virtual content is displayed within lenses of the glasses while a user views a real-world environment through the lenses. For example, an image can be presented on a transparent display that allows a user to simultaneously view content presented on the display and real-world objects.

The messaging server system 108 provides server-side functionality via the network 112 to a particular messaging client 104. While certain functions of the messaging system 100 are described herein as being performed by either a messaging client 104 (or EMG communication device 119) or by the messaging server system 108, the location of certain functionality either within the messaging client 104 or the messaging server system 108 may be a design choice. For example, it may be technically preferable to initially deploy certain technology and functionality within the messaging server system 108 but to later migrate this technology and functionality to the messaging client 104 (or EMG communication device 119) where a client device 102 (or EMG communication device 119) has sufficient processing capacity.

The messaging server system 108 supports various services and operations that are provided to the messaging client 104. Such operations include transmitting data to, receiving data from, and processing data generated by the messaging client 104. This data may include message content, client device information, geolocation information, media augmentation and overlays, message content persistence conditions, social network information, and live event information, as examples. Data exchanges within the messaging system 100 are invoked and controlled through functions available via user interfaces of the messaging client 104.

Turning now specifically to the messaging server system 108, an API server 116 is coupled to, and provides a programmatic interface to, application servers 114. The application servers 114 are communicatively coupled to a database server 120, which facilitates access to a database 126 that stores data associated with messages processed by the application servers 114. Similarly, a web server 128 is coupled to the application servers 114, and provides web-based interfaces to the application servers 114. To this end, the web server 128 processes incoming network requests over the Hypertext Transfer Protocol (HTTP) and several other related protocols.

The API server 116 receives and transmits message data (e.g., commands and message payloads) between the client device 102 and the application servers 114. Specifically, the API server 116 provides a set of interfaces (e.g., routines and protocols) that can be called or queried by the messaging client 104 in order to invoke functionality of the application servers 114. The API server 116 exposes various functions supported by the application servers 114, including account registration, login functionality, the sending of messages, via the application servers 114, from a particular messaging client 104 to another messaging client 104, the sending of media files (e.g., images or video) from a messaging client 104 to a messaging server 118, and for possible access by another messaging client 104, the settings of a collection of media data (e.g., story), the retrieval of a list of friends of a user of a client device 102, the retrieval of such collections, the retrieval of messages and content, the addition and deletion of entities (e.g., friends) to an entity graph (e.g., a social graph), the location of friends within a social graph, opening an application event (e.g., relating to the messaging client 104), and transmission of EMG communications or EMG signals obtained from an EMG communication device 119.

The application servers 114 host several server applications and subsystems, including for example a messaging server 118, an image processing server 122, and a social network server 124. The messaging server 118 implements a number of message processing technologies and functions, particularly related to the aggregation and other processing of content (e.g., textual and multimedia content) included in messages received from multiple instances of the messaging client 104. As will be described in further detail, the text and media content from multiple sources may be aggregated into collections of content (e.g., called stories or galleries). These collections are then made available to the messaging client 104. Other processor- and memory-intensive processing of data may also be performed server-side by the messaging server 118, in view of the hardware requirements for such processing.

The application servers 114 also include an image processing server 122 that is dedicated to performing various image processing operations, typically with respect to images or video within the payload of a message sent from or received at the messaging server 118.

Image processing server 122 is used to implement scan functionality of the augmentation system 208. Scan functionality includes activating and providing one or more augmented reality experiences on a client device 102 when an image is captured by the client device 102. Specifically, the messaging client 104 on the client device 102 can be used to activate a camera. The camera displays one or more real-time images or a video to a user along with one or more icons or identifiers of one or more augmented reality experiences. The user can select a given one of the identifiers to launch the corresponding augmented reality experience. Launching the augmented reality experience includes obtaining one or more augmented reality items associated with the augmented reality experience and overlaying the augmented reality items on top of the images or video being presented.

Figure 3:
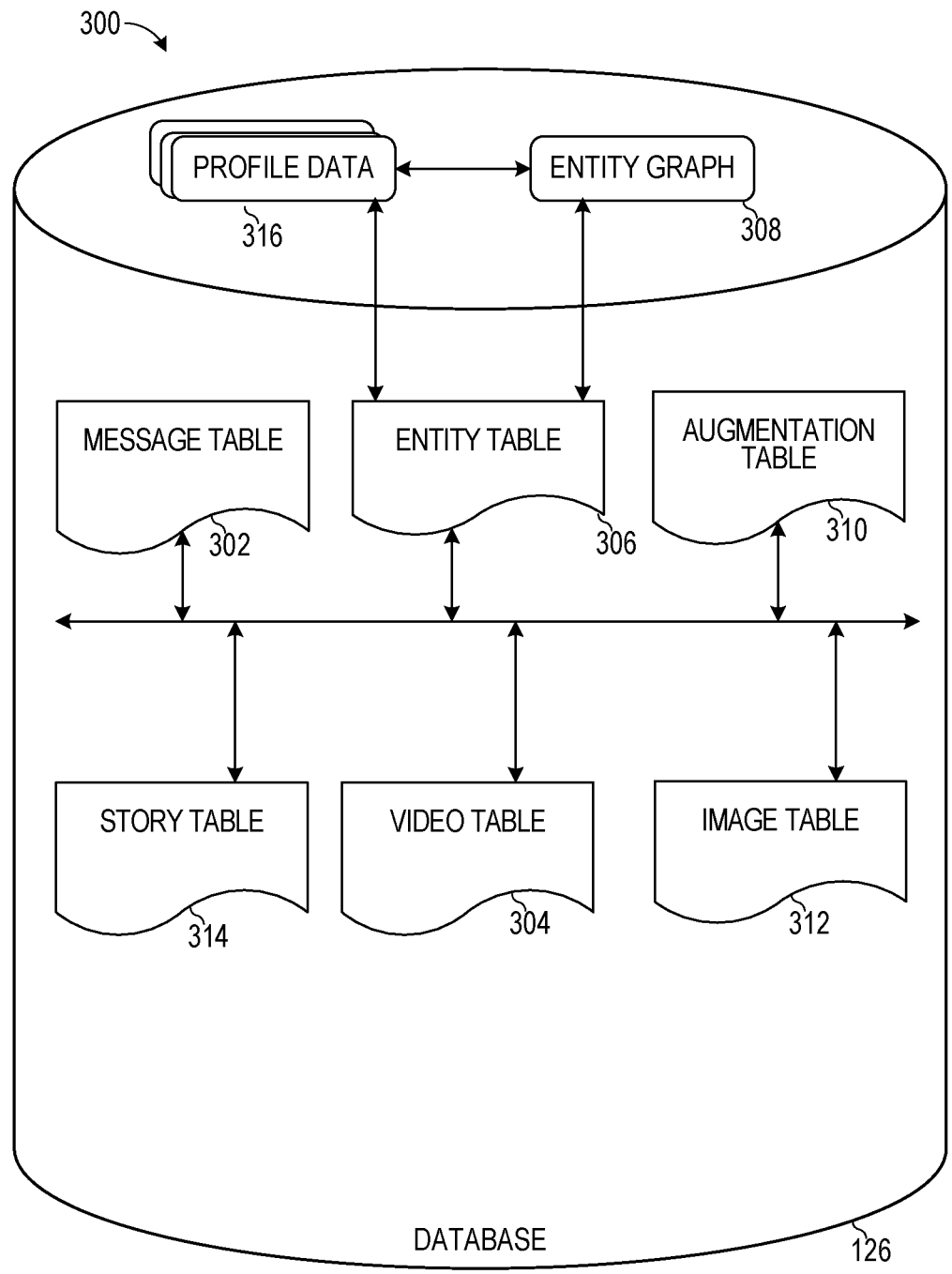
FIG. 3 is a diagrammatic representation of a data structure as maintained in a database, in accordance with some examples.

The social network server 124 supports various social networking functions and services and makes these functions and services available to the messaging server 118. To this end, the social network server 124 maintains and accesses an entity graph 308 (as shown in FIG. 3) within the database 126. Examples of functions and services supported by the social network server 124 include the identification of other users of the messaging system 100 with which a particular user has relationships or is "following," and also the identification of other entities and interests of a particular user.

Returning to the messaging client 104, features and functions of an external resource (e.g., a third-party application 109 or applet) are made available to a user via an interface of the messaging client 104. The messaging client 104 receives a user selection of an option to launch or access features of an external resource (e.g., a third-party resource), such as external apps 109. The external resource may be a third-party application (external apps 109) installed on the client device 102 (e.g., a "native app"), or a small-scale version of the third-party application (e.g., an "applet") that is hosted on the client device 102 or remote of the client device 102 (e.g., on third-party servers 110). The small-scale version of the third-party application includes a subset of features and functions of the third-party application (e.g., the full-scale, native version of the third-party standalone application) and is implemented using a markup-language document. In some examples, the small-scale version of the third-party application (e.g., an "applet") is a web-based, markup-language version of the third-party application and is embedded in the messaging client 104. In addition to using markup-language documents (e.g., a .*ml file), an applet may incorporate a scripting language (e.g., a .*js file or a .json file) and a style sheet (e.g., a .*ss file).

In response to receiving a user selection of the option to launch or access features of the external resource (external app 109), the messaging client 104 determines whether the selected external resource is a web-based external resource or a locally-installed external application. In some cases, external applications 109 that are locally installed on the client device 102 can be launched independently of and separately from the messaging client 104, such as by selecting an icon, corresponding to the external application 109, on a home screen of the client device 102. Small-scale versions of such external applications can be launched or accessed via the messaging client 104 and, in some examples, no or limited portions of the small-scale external application can be accessed outside of the messaging client 104. The small-scale external application can be launched by the messaging client 104 receiving, from an external app(s) server 110, a markup-language document associated with the small-scale external application and processing such a document.

In response to determining that the external resource is a locally-installed external application 109, the messaging client 104 instructs the client device 102 to launch the external application 109 by executing locally-stored code corresponding to the external application 109. In response to determining that the external resource is a web-based resource, the messaging client 104 communicates with the external app(s) servers 110 to obtain a markup-language document corresponding to the selected resource. The messaging client 104 then processes the obtained markup-language document to present the web-based external resource within a user interface of the messaging client 104.

The messaging client 104 can notify a user of the client device 102, or other users related to such a user (e.g., "friends"), of activity taking place in one or more external resources. For example, the messaging client 104 can provide participants in a conversation (e.g., a chat session) in the messaging client 104 with notifications relating to the current or recent use of an external resource by one or more members of a group of users. One or more users can be invited to join in an active external resource or to launch a recently-used but currently inactive (in the group of friends)

external resource. The external resource can provide participants in a conversation, each using a respective messaging client messaging clients 104, with the ability to share an item, status, state, or location in an external resource with one or more members of a group of users into a chat session. The shared item may be an interactive chat card with which members of the chat can interact, for example, to launch the corresponding external resource, view specific information within the external resource, or take the member of the chat to a specific location or state within the external resource. Within a given external resource, response messages can be sent to users on the messaging client 104. The external resource can selectively include different media items in the responses, based on a current context of the external resource.

The messaging client 104 can present a list of the available external resources (e.g., third-party or external applications 109 or applets) to a user to launch or access a given external resource. This list can be presented in a context-sensitive menu. For example, the icons representing different ones of the external application 109 (or applets) can vary based on how the menu is launched by the user (e.g., from a conversation interface or from a non-conversation interface).

In some examples, the messaging client 104 can present an option to communicate or compose a message or control other features (e.g., AR features) of the messaging client 104 using EMG signals. In such cases, the messaging client 104 communicates with the EMG communication device 119 and instructs the EMG communication device 119 to begin collecting EMG signals, such as via one or more EMG electrodes. The EMG communication device 119 can collect EMG signals representing silent speech and provide such signals to the messaging client 104. In some examples, the EMG communication device 119 can filter out interfering signals (e.g., eye blinks and/or involuntary gestures) from the EMG signals.

System Architecture

Figure 2:
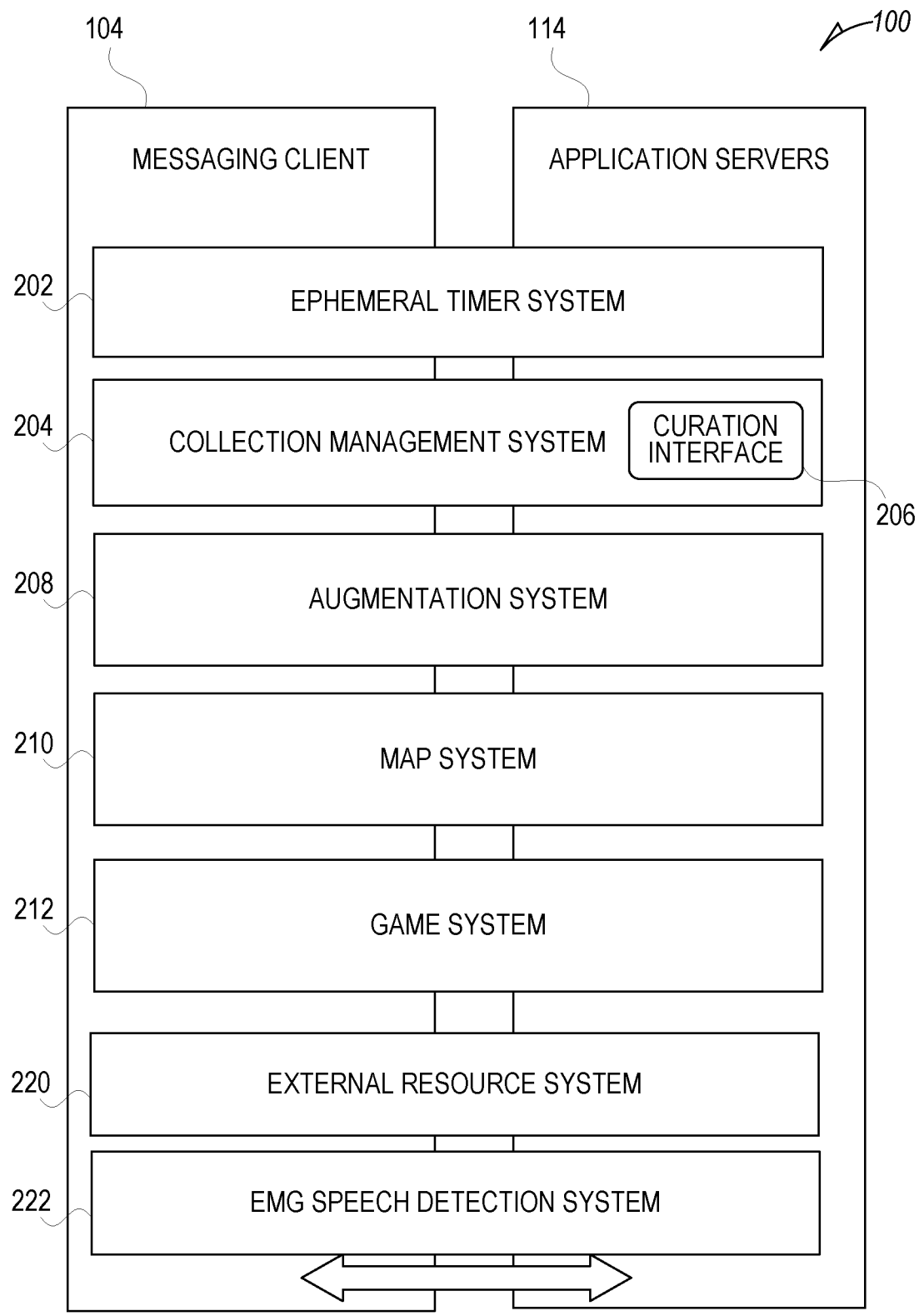
FIG. 2 is a diagrammatic representation of a messaging system, in accordance with some examples, that has both client-side and server-side functionality.

FIG. 2 is a diagrammatic representation of a messaging system 100, in accordance with some examples, that has both client-side and server-side functionality. Specifically, the messaging system 100 is shown to comprise the messaging client 104 and the application servers 114. The messaging system 100 embodies several subsystems, which are supported on the client-side by the messaging client 104 and on the server-side by the application servers 114. These subsystems include, for example, an ephemeral timer system 202, a collection management system 204, an augmentation system 208, a map system 210, a game system 212, an external resource system 220, and an EMG speech detection system 222.

The ephemeral timer system 202 is responsible for enforcing the temporary or time-limited access to content by the messaging client 104 and the messaging server 118. The ephemeral timer system 202 incorporates several timers that, based on duration and display parameters associated with a message, or collection of messages (e.g., a story), selectively enable access (e.g., for presentation and display) to messages and associated content via the messaging client 104. Further details regarding the operation of the ephemeral timer system 202 are provided below.

The collection management system 204 is responsible for managing sets or collections of media (e.g., collections of text, image video, and audio data). A collection of content (e.g., messages, including images, video, text, and audio) may be organized into an "event gallery" or an "event story." Such a collection may be made available for a specified time period, such as the duration of an event to which the content relates. For example, content relating to a music concert may be made available as a "story" for the duration of that music concert. The collection management system 204 may also be responsible for publishing an icon that provides notification of the existence of a particular collection to the user interface of the messaging client 104.

The collection management system 204 furthermore includes a curation interface 206 that allows a collection manager to manage and curate a particular collection of content. For example, the curation interface 206 enables an event organizer to curate a collection of content relating to a specific event (e.g., delete inappropriate content or redundant messages). Additionally, the collection management system 204 employs machine vision (or image recognition technology) and content rules to automatically curate a content collection. In certain examples, compensation may be paid to a user for the inclusion of user-generated content into a collection. In such cases, the collection management system 204 operates to automatically make payments to such users for the use of their content.

The augmentation system 208 provides various functions that enable a user to augment (e.g., annotate or otherwise modify or edit) media content associated with a message. For example, the augmentation system 208 provides functions related to the generation and publishing of media overlays for messages processed by the messaging system 100. The augmentation system 208 operatively supplies a media overlay or augmentation (e.g., an image filter) to the messaging client 104 based on a geolocation of the client device 102. In another example, the augmentation system 208 operatively supplies a media overlay to the messaging client 104 based on other information, such as social network information of the user of the client device 102. A media overlay may include audio and visual content and visual effects. Examples of audio and visual content include pictures, texts, logos, animations, and sound effects. An example of a visual effect includes color overlaying. The audio and visual content or the visual effects can be applied to a media content item (e.g., a photo) at the client device 102. For example, the media overlay may include text, a graphical element, or image that can be overlaid on top of a photograph taken by the client device 102. In another example, the media overlay includes an identification of a location overlay (e.g., Venice beach), a name of a live event, or a name of a merchant overlay (e.g., Beach Coffee House). In another example, the augmentation system 208 uses the geolocation of the client device 102 to identify a media overlay that includes the name of a merchant at the geolocation of the client device 102. The media overlay may include other indicia associated with the merchant. The media overlays may be stored in the database 126 and accessed through the database server 120.

In some examples, the augmentation system 208 provides a user-based publication platform that enables users to select a geolocation on a map and upload content associated with the selected geolocation. The user may also specify circumstances under which a particular media overlay should be offered to other users. The augmentation system 208 generates a media overlay that includes the uploaded content and associates the uploaded content with the selected geolocation.

In some examples, the augmentation system 208 provides a merchant-based publication platform that enables merchants to select a particular media overlay associated with a geolocation via a bidding process. For example, the augmentation system 208 associates the media overlay of the highest bidding merchant with a corresponding geolocation for a predefined amount of time. The augmentation system 208 communicates with the image processing server 122 to obtain augmented reality experiences and presents identifiers of such experiences in one or more user interfaces (e.g., as icons over a real-time image or video or as thumbnails or icons in interfaces dedicated for presented identifiers of augmented reality experiences). Once an augmented reality experience is selected, one or more images, videos, or augmented reality graphical elements are retrieved and presented as an overlay on top of the images or video captured by the client device 102. In some cases, the camera is switched to a front-facing view (e.g., the front-facing camera of the client device 102 is activated in response to activation of a particular augmented reality experience) and the images from the front-facing camera of the client device 102 start being displayed on the client device 102 instead of the rear-facing camera of the client device 102. The one or more images, videos, or augmented reality graphical elements are retrieved and presented as an overlay on top of the images that are captured and displayed by the front-facing camera of the client device 102.

The map system 210 provides various geographic location functions, and supports the presentation of map-based media content and messages by the messaging client 104. For example, the map system 210 enables the display of user icons or avatars (e.g., stored in profile data 316) on a map to indicate a current or past location of "friends" of a user, as well as media content (e.g., collections of messages including photographs and videos) generated by such friends, within the context of a map. For example, a message posted by a user to the messaging system 100 from a specific geographic location may be displayed within the context of a map at that particular location to "friends" of a specific user on a map interface of the messaging client 104. A user can furthermore share his or her location and status information (e.g., using an appropriate status avatar) with other users of the messaging system 100 via the messaging client 104, with this location and status information being similarly displayed within the context of a map interface of the messaging client 104 to selected users.

The game system 212 provides various gaming functions within the context of the messaging client 104. The messaging client 104 provides a game interface providing a list of available games (e.g., web-based games or web-based applications) that can be launched by a user within the context of the messaging client 104, and played with other users of the messaging system 100. The messaging system 100 further enables a particular user to invite other users to participate in the play of a specific game, by issuing invitations to such other users from the messaging client 104. The messaging client 104 also supports both voice and text messaging (e.g., chats) within the context of gameplay, provides a leaderboard for the games, and also supports the provision of in-game rewards (e.g., coins and items).

The external resource system 220 provides an interface for the messaging client 104 to communicate with external app(s) servers 110 to launch or access external resources. Each external resource (apps) server 110 hosts, for example, a markup language (e.g., HTML5) based application or small-scale version of an external application (e.g., game, utility, payment, or ride-sharing application that is external to the messaging client 104). The messaging client 104 may launch a web-based resource (e.g., application) by accessing the HTML5 file from the external resource (apps) servers 110 associated with the web-based resource. In certain examples, applications hosted by external resource servers 110 are programmed in JavaScript leveraging a Software Development Kit (SDK) provided by the messaging server 118. The SDK includes Application Programming Interfaces (APIs) with functions that can be called or invoked by the web-based application. In certain examples, the messaging server 118 includes a JavaScript library that provides a given third-party resource access to certain user data of the messaging client 104. HTML5 is used as an example technology for programming games, but applications and resources programmed based on other technologies can be used.

To integrate the functions of the SDK into the web-based resource, the SDK is downloaded by an external resource (apps) server 110 from the messaging server 118 or is otherwise received by the external resource (apps) server 110. Once downloaded or received, the SDK is included as part of the application code of a web-based external resource. The code of the web-based resource can then call or invoke certain functions of the SDK to integrate features of the messaging client 104 into the web-based resource.

The SDK stored on the messaging server 118 effectively provides the bridge between an external resource (e.g., third-party or external applications 109 or applets and the messaging client 104). This provides the user with a seamless experience of communicating with other users on the messaging client 104, while also preserving the look and feel of the messaging client 104. To bridge communications between an external resource and a messaging client 104, in certain examples, the SDK facilitates communication between external resource servers 110 and the messaging client 104. In certain examples, a Web ViewJavaScript-Bridge running on a client device 102 establishes two one-way communication channels between an external resource and the messaging client 104. Messages are sent between the external resource and the messaging client 104 via these communication channels asynchronously. Each SDK function invocation is sent as a message and callback. Each SDK function is implemented by constructing a unique callback identifier and sending a message with that callback identifier.

By using the SDK, not all information from the messaging client 104 is shared with external resource servers 110. The SDK limits which information is shared based on the needs of the external resource. In certain examples, each external resource server 110 provides an HTML5 file corresponding to the web-based external resource to the messaging server 118. The messaging server 118 can add a visual representation (such as a box art or other graphic) of the web-based external resource in the messaging client 104. Once the user selects the visual representation or instructs the messaging client 104 through a GUI of the messaging client 104 to access features of the web-based external resource, the messaging client 104 obtains the HTML5 file and instantiates the resources necessary to access the features of the web-based external resource.

The messaging client 104 presents a graphical user interface (e.g., a landing page or title screen) for an external resource. During, before, or after presenting the landing page or title screen, the messaging client 104 determines whether the launched external resource has been previously authorized to access user data of the messaging client 104. In response to determining that the launched external resource has been previously authorized to access user data of the messaging client 104, the messaging client 104 presents another graphical user interface of the external resource that includes functions and features of the external resource. In response to determining that the launched external resource has not been previously authorized to access user data of the messaging client 104, after a threshold period of time (e.g., 3 seconds) of displaying the landing page or title screen of the external resource, the messaging client 104 slides up (e.g., animates a menu as surfacing from a bottom of the screen to a middle of or other portion of the screen) a menu for authorizing the external resource to access the user data. The menu identifies the type of user data that the external resource will be authorized to use. In response to receiving a user selection of an accept option, the messaging client 104 adds the external resource to a list of authorized external resources and allows the external resource to access user data from the messaging client 104. In some examples, the external resource is authorized by the messaging client 104 to access the user data in accordance with an OAuth 2 framework.

The messaging client 104 controls the type of user data that is shared with external resources based on the type of external resource being authorized. For example, external resources that include full-scale external applications (e.g., a third-party or external application 109) are provided with access to a first type of user data (e.g., only two-dimensional avatars of users with or without different avatar characteristics). As another example, external resources that include small-scale versions of external applications (e.g., web-based versions of third-party applications) are provided with access to a second type of user data (e.g., payment information, two-dimensional avatars of users, three-dimensional avatars of users, and avatars with various avatar characteristics). Avatar characteristics include different ways to customize a look and feel of an avatar, such as different poses, facial features, clothing, and so forth.

The EMG speech detection system 222 can be implemented in whole or in part by the messaging client 104, the application servers 114, and the EMG communication device 119. The EMG speech detection system 222 is configured to collect EMG signals from the EMG communication device 119. Specifically, the EMG speech detection system 222 can detect or receive data from one or more EMG electrodes of EMG communication device 119. The data represents subthreshold (or above threshold) muscle activation signals of one or more muscles associated with speech production of a user. The subthreshold (or above threshold) muscle activation signals can be generated as a result of, and in response to, inner speech (e.g., silent speech) of a user. Namely, a user can activate the EMG speech detection system 222, such as by speaking a command (or saying the command via inner speech) or pressing a suitable button or selecting an option. After activating the EMG speech detection system 222, the user can imagine speaking a word or phrase without actually moving any muscles (e.g., larynx or throat muscles) used to produce speech. When the user imagines speaking the word or phrase, subthreshold muscle activation signals are transmitted from the motor cortex to the muscles used to produce speech, but the signals are not strong enough to actually cause the muscles to move.

The EMG communication device 119 (which can be a collar worn around a front or back of the neck of the user) can detect and receive the subthreshold muscle activation signals. The EMG communication device 119 and/or the EMG speech detection system 222 can process the detected subthreshold muscle activation signals by applying a machine learning technique (e.g., machine learning model, such as a neural network) to the subthreshold muscle activation signals to estimate one or more speech features corresponding to the subthreshold muscle activation signals. The machine learning technique can be trained to establish a relationship between a plurality of training subthreshold muscle activation signals and ground truth speech features. The EMG speech detection system 222 can then generate visual or audible output based on the one or more speech features, such as by applying another machine learning technique (or other neural network) to the one or more speech features. The EMG speech detection system 222 can then cause the visual or audible output to be processed by a messaging application to engage a feature of the messaging application.

In some examples, prior to applying the machine learning technique to the subthreshold muscle activation signals, the EMG communication device 119 filters out or removes interfering signals (such as eye blinks or other involuntary physical movements performed while the inner speech signals are collected). To remove the interfering signals, the EMG communication device 119 can perform a set of operations including applying a transform (e.g., an independent component analysis (ICA) transform) to the subthreshold muscle activation signals detected by the plurality of EMG electrodes of the EMG communication device 119 to represent the subthreshold muscle activation signals as a plurality of maximally independent components. The EMG communication device 119 can access an interference template corresponding to an eye blink component and can filter the plurality of maximally independent components based on the interference template to provide filtered maximally independent components. For example, the EMG communication device 119 can find one of the ICA components that closely matches or has a high degree of correlation to the eye blink component and can set that ICA component to a low value, such as zero. Then, the EMG communication device 119 can regenerate a filtered version of the subthreshold muscle activation signals based on the filtered maximally independent components, such as by applying an inverse transform (e.g., an inverse ICA transform) to the filtered version of the subthreshold muscle activation signals. This filtered version of the subthreshold muscle activation signals can be processed by the machine learning technique to estimate one or more speech features corresponding to the filtered version of the subthreshold muscle activation signals.

In some examples, the EMG speech detection system 222 can synthesize the one or more speech features into a spoken output or verbal output to generate a voice message for transmission to another user. In some examples, the EMG speech detection system 222 can generate a text message that includes text corresponding to the one or more speech features for transmission to another user. In some examples, the EMG speech detection system 222 can generate an instructions that can control AR/VR components of the client device 102 based on the one or more speech features.

In some cases, the EMG speech detection system 222 can apply a calibration process on a per-user basis to generate the eye blink component (or other component representing involuntary physical gestures or movements). In some examples, the calibration process can be started in response to a command received from a user wearing or using the EMG communication device 119. The calibration process can involve collecting a plurality of training data from a particular user, wearing the EMG communication device 119, that includes a set of subthreshold muscle activation signals and a training set of ground truth eye blink components. Specifically, the set of subthreshold muscle activation signals can be transformed using an ICA transform into ICA components. From the ICA components, a given ICA component corresponding to an eye blink can be automatically or manually specified and used as the ground truth eye blink component. A machine learning model can be applied to the set of subthreshold muscle activation signals to generate an estimated eye blink component. A deviation between the estimated eye blink component and the ground truth eye blink component associated with the first subthreshold muscle activation signal can be computed and used to update one or more parameters of the machine learning model.

Further features of the EMG speech detection system 222 and the EMG communication device 119 are described below in connection with FIGS. 5-9.

Data Architecture

FIG. 3 is a schematic diagram illustrating data structures 300, which may be stored in the database 126 of the messaging server system 108, according to certain examples. While the content of the database 126 is shown to comprise a number of tables, it will be appreciated that the data could be stored in other types of data structures (e.g., as an object-oriented database).

The database 126 includes message data stored within a message table 302. This message data includes, for any particular one message, at least message sender data, message recipient (or receiver) data, and a payload. Further details regarding information that may be included in a message, and included within the message data stored in the message table 302, are described below with reference to FIG. 4.

An entity table 306 stores entity data, and is linked (e.g., referentially) to an entity graph 308 and profile data 316. Entities for which records are maintained within the entity table 306 may include individuals, corporate entities, organizations, objects, places, events, and so forth. Regardless of entity type, any entity regarding which the messaging server system 108 stores data may be a recognized entity. Each entity is provided with a unique identifier, as well as an entity type identifier (not shown).

The entity graph 308 stores information regarding relationships and associations between entities. Such relationships may be social, professional (e.g., work at a common corporation or organization) interested-based or activity-based, merely for example.

The profile data 316 stores multiple types of profile data about a particular entity. The profile data 316 may be selectively used and presented to other users of the messaging system 100, based on privacy settings specified by a particular entity. Where the entity is an individual, the profile data 316 includes, for example, a user name, telephone number, address, settings (e.g., notification and privacy settings), as well as a user-selected avatar representation (or collection of such avatar representations). A particular user may then selectively include one or more of these avatar representations within the content of messages communicated via the messaging system 100, and on map interfaces displayed by messaging clients 104 to other users. The collection of avatar representations may include "status avatars," which present a graphical representation of a status or activity that the user may select to communicate at a particular time.

Where the entity is a group, the profile data 316 for the group may similarly include one or more avatar representations associated with the group, in addition to the group name, members, and various settings (e.g., notifications) for the relevant group.

The database 126 also stores augmentation data, such as overlays or filters, in an augmentation table 310. The augmentation data is associated with and applied to videos (for which data is stored in a video table 304) and images (for which data is stored in an image table 312).

Filters, in some examples, are overlays that are displayed as overlaid on an image or video during presentation to a recipient user. Filters may be of various types, including user-selected filters from a set of filters presented to a sending user by the messaging client 104 when the sending user is composing a message. Other types of filters include geolocation filters (also known as geo-filters), which may be presented to a sending user based on geographic location. For example, geolocation filters specific to a neighborhood or special location may be presented within a user interface by the messaging client 104, based on geolocation information determined by a Global Positioning System (GPS) unit of the client device 102.

Another type of filter is a data filter, which may be selectively presented to a sending user by the messaging client 104, based on other inputs or information gathered by the client device 102 during the message creation process. Examples of data filters include current temperature at a specific location, a current speed at which a sending user is traveling, battery life for a client device 102, or the current time.

Other augmentation data that may be stored within the image table 312 includes augmented reality content items (e.g., corresponding to applying augmented reality experiences). An augmented reality content item or augmented reality item may be a real-time special effect and sound that may be added to an image or a video.

As described above, augmentation data includes augmented reality content items, overlays, image transformations, AR images, and similar terms that refer to modifications that may be applied to image data (e.g., videos or images). This includes real-time modifications, which modify an image as it is captured using device sensors (e.g., one or multiple cameras) of a client device 102 and then displayed on a screen of the client device 102 with the modifications. This also includes modifications to stored content, such as video clips in a gallery that may be modified. For example, in a client device 102 with access to multiple augmented reality content items, a user can use a single video clip with multiple augmented reality content items to see how the different augmented reality content items will modify the stored clip. For example, multiple augmented reality content items that apply different pseudorandom movement models can be applied to the same content by selecting different augmented reality content items for the content. Similarly, real-time video capture may be used with an illustrated modification to show how video images currently being captured by sensors of a client device 102 would modify the captured data. Such data may simply be displayed on the screen and not stored in memory, or the content captured by the device sensors may be recorded and stored in memory with or without the modifications (or both). In some systems, a preview feature can show how different augmented reality content items will look within different windows in a display at the same time. This can, for example, enable multiple windows with different pseudorandom animations to be viewed on a display at the same time.

Data and various systems using augmented reality content items or other such transform systems to modify content using this data can thus involve detection of objects (e.g., faces, hands, bodies, cats, dogs, surfaces, objects, etc.), tracking of such objects as they leave, enter, and move around the field of view in video frames, and the modification or transformation of such objects as they are tracked. In various examples, different methods for achieving such transformations may be used. Some examples may involve generating a three-dimensional mesh model of the object or objects, and using transformations and animated textures of the model within the video to achieve the transformation. In some examples, tracking of points on an object may be used to place an image or texture (which may be two-dimensional or three-dimensional) at the tracked position. In still further examples, neural network analysis of video frames may be used to place images, models, or textures in content (e.g., images or frames of video). Augmented reality content items thus refer both to the images, models, and textures used to create transformations in content, as well as to additional modeling and analysis information needed to achieve such transformations with object detection, tracking, and placement.

Real-time video processing can be performed with any kind of video data (e.g., video streams, video files, etc.) saved in a memory of a computerized system of any kind. For example, a user can load video files and save them in a memory of a device, or can generate a video stream using sensors of the device. Additionally, any objects can be processed using a computer animation model, such as a human's face and parts of a human body, animals, or non-living things such as chairs, cars, or other objects.

In some examples, when a particular modification is selected along with content to be transformed, elements to be transformed are identified by the computing device, and then detected and tracked if they are present in the frames of the video. The elements of the object are modified according to the request for modification, thus transforming the frames of the video stream. Transformation of frames of a video stream can be performed by different methods for different kinds of transformation. For example, for transformations of frames mostly referring to changing forms of object's elements, characteristic points for each element of an object are calculated (e.g., using an Active Shape Model (ASM) or other known methods). Then, a mesh based on the characteristic points is generated for each of the at least one element of the object. This mesh is used in the following stage of tracking the elements of the object in the video stream. In the process of tracking, the mentioned mesh for each element is aligned with a position of each element. Then, additional points are generated on the mesh. A first set of first points is generated for each element based on a request for modification, and a set of second points is generated for each element based on the set of first points and the request for modification. Then, the frames of the video stream can be transformed by modifying the elements of the object on the basis of the sets of first and second points and the mesh. In such a method, a background of the modified object can be changed or distorted as well by tracking and modifying the background.

In some examples, transformations changing some areas of an object using its elements can be performed by calculating characteristic points for each element of an object and generating a mesh based on the calculated characteristic points. Points are generated on the mesh, and then various areas based on the points are generated. The elements of the object are then tracked by aligning the area for each element with a position for each of the at least one element, and properties of the areas can be modified based on the request for modification, thus transforming the frames of the video stream. Depending on the specific request for modification, properties of the mentioned areas can be transformed in different ways. Such modifications may involve changing color of areas; removing at least some part of areas from the frames of the video stream; including one or more new objects into areas which are based on a request for modification; and modifying or distorting the elements of an area or object. In various examples, any combination of such modifications or other similar modifications may be used. For certain models to be animated, some characteristic points can be selected as control points to be used in determining the entire state-space of options for the model animation.

In some examples of a computer animation model to transform image data using face detection, the face is detected on an image with use of a specific face detection algorithm (e.g., Viola-Jones). Then, an Active Shape Model (ASM) algorithm is applied to the face region of an image to detect facial feature reference points.

Other methods and algorithms suitable for face detection can be used. For example, in some examples, features are located using a landmark, which represents a distinguishable point present in most of the images under consideration. For facial landmarks, for example, the location of the left eye pupil may be used. If an initial landmark is not identifiable (e.g., if a person has an eyepatch), secondary landmarks may be used. Such landmark identification procedures may be used for any such objects. In some examples, a set of landmarks forms a shape. Shapes can be represented as vectors using the coordinates of the points in the shape. One shape is aligned to another with a similarity transform (allowing translation, scaling, and rotation) that minimizes the average Euclidean distance between shape points. The mean shape is the mean of the aligned training shapes.

In some examples, a search is started for landmarks from the mean shape aligned to the position and size of the face determined by a global face detector. Such a search then repeats the steps of suggesting a tentative shape by adjusting the locations of shape points by template matching of the image texture around each point and then conforming the tentative shape to a global shape model until convergence occurs. In some systems, individual template matches are unreliable, and the shape model pools the results of the weak template matches to form a stronger overall classifier. The entire search is repeated at each level in an image pyramid, from coarse to fine resolution.

A transformation system can capture an image or video stream on a client device (e.g., the client device 102) and perform complex image manipulations locally on the client device 102 while maintaining a suitable user experience, computation time, and power consumption. The complex image manipulations may include size and shape changes, emotion transfers (e.g., changing a face from a frown to a smile), state transfers (e.g., aging a subject, reducing apparent age, changing gender), style transfers, graphical element application, and any other suitable image or video manipulation implemented by a convolutional neural network that has been configured to execute efficiently on the client device 102.

In some examples, a computer animation model to transform image data can be used by a system where a user may capture an image or video stream of the user (e.g., a selfie) using a client device 102 having a neural network operating as part of a messaging client 104 operating on the client device 102. The transformation system operating within the messaging client 104 determines the presence of a face within the image or video stream and provides modification icons associated with a computer animation model to transform image data, or the computer animation model can be present as associated with an interface described herein. The modification icons include changes that may be the basis for modifying the user's face within the image or video stream as part of the modification operation. Once a modification icon is selected, the transformation system initiates a process to convert the image of the user to reflect the selected modification icon (e.g., generate a smiling face on the user). A modified image or video stream may be presented in a graphical user interface displayed on the client device 102 as soon as the image or video stream is captured, and a specified modification is selected. The transformation system may implement a complex convolutional neural network on a portion of the image or video stream to generate and apply the selected modification. That is, the user may capture the image or video stream and be presented with a modified result in real-time or near real-time once a modification icon has been selected. Further, the modification may be persistent while the video stream is being captured, and the selected modification icon remains toggled. Machine-taught neural networks may be used to enable such modifications.

The graphical user interface, presenting the modification performed by the transformation system, may supply the user with additional interaction options. Such options may be based on the interface used to initiate the content capture and selection of a particular computer animation model (e.g., initiation from a content creator user interface). In various examples, a modification may be persistent after an initial selection of a modification icon. The user may toggle the modification on or off by tapping or otherwise selecting the face being modified by the transformation system and store it for later viewing or browsing to other areas of the imaging application. Where multiple faces are modified by the transformation system, the user may toggle the modification on or off globally by tapping or selecting a single face modified and displayed within a graphical user interface. In some examples, individual faces, among a group of multiple faces, may be individually modified, or such modifications may be individually toggled by tapping or selecting the individual face or a series of individual faces displayed within the graphical user interface.

A story table 314 stores data regarding collections of messages and associated image, video, or audio data, which are compiled into a collection (e.g., a story or a gallery). The creation of a particular collection may be initiated by a particular user (e.g., each user for which a record is maintained in the entity table 306). A user may create a "personal story" in the form of a collection of content that has been created and sent/broadcast by that user. To this end, the user interface of the messaging client 104 may include an icon that is user-selectable to enable a sending user to add specific content to his or her personal story.

A collection may also constitute a "live story," which is a collection of content from multiple users that is created manually, automatically, or using a combination of manual and automatic techniques. For example, a "live story" may constitute a curated stream of user-submitted content from various locations and events. Users whose client devices have location services enabled and are at a common location event at a particular time may, for example, be presented with an option, via a user interface of the messaging client 104, to contribute content to a particular live story. The live story may be identified to the user by the messaging client 104, based on his or her location. The end result is a "live story" told from a community perspective.

A further type of content collection is known as a "location story," which enables a user whose client device 102 is located within a specific geographic location (e.g., on a college or university campus) to contribute to a particular collection. In some examples, a contribution to a location story may require a second degree of authentication to verify that the end user belongs to a specific organization or other entity (e.g., is a student on the university campus).

As mentioned above, the video table 304 stores video data that, in some examples, is associated with messages for which records are maintained within the message table 302. Similarly, the image table 312 stores image data associated with messages for which message data is stored in the entity table 306. The entity table 306 may associate various augmentations from the augmentation table 310 with various images and videos stored in the image table 312 and the video table 304.

Data Communications Architecture

Figure 4:
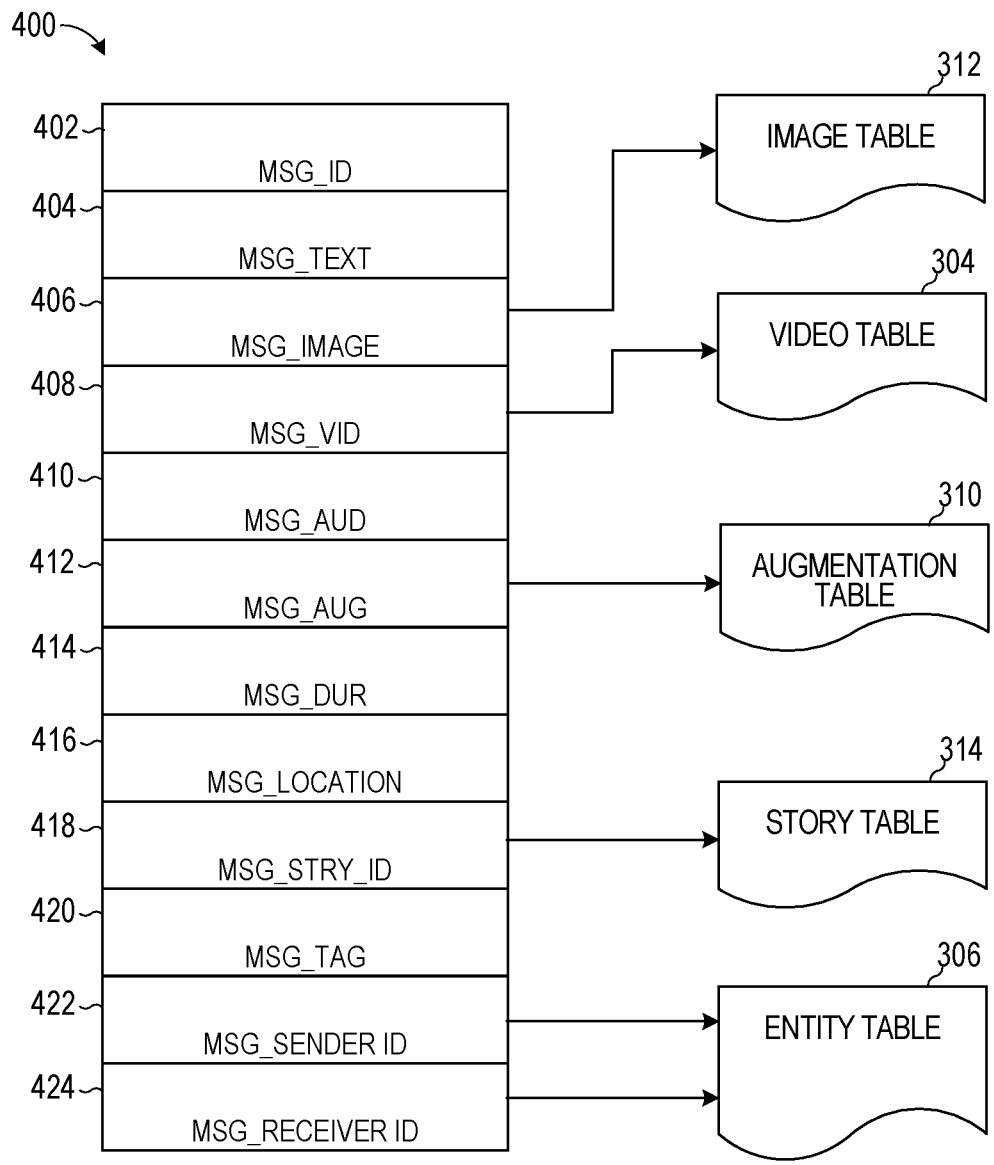
FIG. 4 is a diagrammatic representation of a message, in accordance with some examples.

FIG. 4 is a schematic diagram illustrating a structure of a message 400, according to some examples, generated by a messaging client 104 for communication to a further messaging client 104 or the messaging server 118. The content of a particular message 400 is used to populate the message table 302 stored within the database 126, accessible by the messaging server 118. Similarly, the content of a message 400 is stored in memory as "in-transit" or "in-flight" data of the client device 102 or the application servers 114. A message 400 is shown to include the following example components:

message identifier 402: a unique identifier that identifies the message 400.

message text payload 404: text, to be generated by a user via a user interface of the client device 102, and that is included in the message 400.

message image payload 406: image data, captured by a camera component of a client device 102 or retrieved from a memory component of a client device 102, and that is included in the message 400. Image data for a sent or received message 400 may be stored in the image table 312.

message video payload 408: video data, captured by a camera component or retrieved from a memory component of the client device 102, and that is included in the message 400. Video data for a sent or received message 400 may be stored in the video table 304.

message audio payload 410: audio data, captured by a microphone or retrieved from a memory component of the client device 102, and that is included in the message 400.

message augmentation data 412: augmentation data (e.g., filters, stickers, or other annotations or enhancements) that represents augmentations to be applied to message image payload 406, message video payload 408, or message audio payload 410 of the message 400. Augmentation data for a sent or received message 400 may be stored in the augmentation table 310.

message duration parameter 414: parameter value indicating, in seconds, the amount of time for which content of the message (e.g., the message image payload 406, message video payload 408, message audio payload 410) is to be presented or made accessible to a user via the messaging client 104.

message geolocation parameter 416: geolocation data (e.g., latitudinal and longitudinal coordinates) associated with the content payload of the message. Multiple message geolocation parameter 416 values may be included in the payload, each of these parameter values being associated with respect to content items included in the content (e.g., a specific image within the message image payload 406, or a specific video in the message video payload 408).

message story identifier 418: identifier values identifying one or more content collections (e.g., "stories" identified in the story table 314) with which a particular content item in the message image payload 406 of the message 400 is associated. For example, multiple images within the message image payload 406 may each be associated with multiple content collections using identifier values.

message tag 420: each message 400 may be tagged with multiple tags, each of which is indicative of the subject matter of content included in the message payload. For example, where a particular image included in the message image payload 406 depicts an animal (e.g., a lion), a tag value may be included within the message tag 420 that is indicative of the relevant animal. Tag values may be generated manually, based on user input, or may be automatically generated using, for example, image recognition.

message sender identifier 422: an identifier (e.g., a messaging system identifier, email address, or device identifier) indicative of a user of the client device 102 on which the message 400 was generated and from which the message 400 was sent.

message receiver identifier 424: an identifier (e.g., a messaging system identifier, email address, or device identifier) indicative of a user of the client device 102 to which the message 400 is addressed.

The contents (e.g., values) of the various components of message 400 may be pointers to locations in tables within which content data values are stored. For example, an image value in the message image payload 406 may be a pointer to (or address of) a location within an image table 312. Similarly, values within the message video payload 408 may point to data stored within a video table 304, values stored within the message augmentation data 412 may point to data stored in an augmentation table 310, values stored within the message story identifier 418 may point to data stored in a story table 314, and values stored within the message sender identifier 422 and the message receiver identifier 424 may point to user records stored within an entity table 306.

EMG Communication Device

Figure 5:
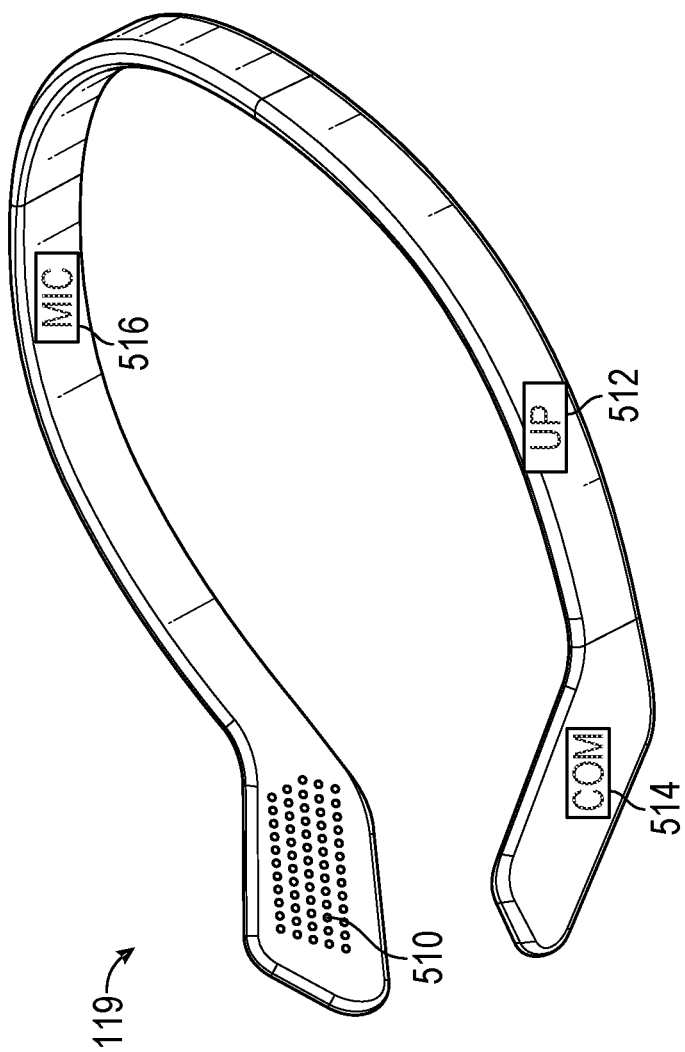
FIGS. 5 and 6 are perspective views of an EMG communication device, in accordance with some examples.

FIG. 5 shows a perspective view of an EMG communication device 119 in the form of a collar that can include the EMG speech detection system 222 according to some examples. The EMG communication device 119 includes a body that can wrap around the back or front of a user's neck. The body includes an array of EMG electrodes 510 on one or both ends of the EMG communication device 119. In this way, when the EMG communication device 119 is worn by a user, a first set of the array of EMG electrodes 510 can capture or detect subthreshold muscle activation signals on a left side of the user's neck, and a second set of the array of EMG electrodes 510 can capture or detect subthreshold muscle activation signals on a right side of the user's neck. The body of the EMG communication device 119 can be made from any suitable material such as plastics or metal, including any suitable shape memory alloy. The body of the EMG communication device 119 can include a touch input interface that is configured to receive touch input from a user (e.g., one finger touch, two finger touch, or combination thereof together) to control operations of the EMG communication device 119, such as to turn the EMG communication device 119 ON/OFF, place the EMG communication device 119 into hibernation mode in which the EMG electrodes 510 are disabled or deactivated to save battery, place the EMG communication device 119 into an active mode in which the EMG electrodes 510 are enabled or activated to detect subthreshold muscle activation signals, and/or a capture mode in which the EMG communication device 119 starts recording the subthreshold muscle activation signals detected by the EMG electrodes 510.

The EMG communication device 119 has onboard electronics components including a computing device, such as a computer 512 or low power processor, which can in different examples be of any suitable type so as to be carried by the body of the EMG communication device 119. In some examples, the computer 512 is at least partially housed in one or both ends of the body of the EMG communication device 119. The computer 512 includes one or more processors with memory (e.g., a volatile storage device, such as random access memory or registers), a storage device (e.g., a non-volatile storage device), and can be in communication with a wireless communication circuitry (e.g., WiFi, BLE communication devices and/or WiFi direct devices) and a power source. The computer 512 can include low-power circuitry, high-speed circuitry, and, in some examples, a display processor. Various examples may include these elements in different configurations or integrated together in different ways.

The computer 512 additionally includes a battery or other suitable portable power supply. In some examples, the battery is disposed in one of the ends of the body of the EMG communication device 119.

The onboard computer 512 and the lenses EMG electrodes 510 are configured together to provide the EMG speech detection system 222 that automatically or selectively captures EMG subthreshold muscle activation signals and converts such signals to visual (e.g., graphics or text) or audible (e.g., verbal or auditory signals) content based on speech features estimated from the subthreshold muscle activation signals. In some examples, the visual and/or audible content is transmitted to the client device 102 and/or to one or more headphones or earbuds worn by a user and/or to a remote server for further processing.

The EMG communication device 119 can include an accelerometer and a touch interface and a voice command system. Based on input received by the EMG communication device 119 from the accelerometer and a touch interface, the EMG communication device 119 can improve calibration and placement of the EMG communication device 119 and the EMG electrodes 510. The EMG communication device 119 can include one or more communication device(s) 514 to communicate with a client device 102 and/or a remote server. The EMG communication device 119 can communicate via the one or more communication device(s) 514, to the client device 102 or the remote server, the raw EMG signals captured by the EMG electrodes 510 and/or processed data and/or speech features estimated from the raw EMG signals captured by the EMG electrodes 510.

The EMG communication device 119 includes a microphone 516 (e.g., bone conductive microphone). The microphone 516 can be used in one or more training modes of the EMG communication device 119 to capture spoken commands and compare such spoken commands to the speech features estimated from the associated EMG signals. The microphone 516 of the EMG communication device 119 can also be used to monitor continuously for a trigger word. The trigger word can instruct the EMG communication device 119 to begin capturing and storing data from the EMG electrodes 510. Namely, the trigger word can be spoken by a user when the user intends to perform inner speech and use the inner speech to control one or more operations of the client device 102 (e.g., a messaging client 104). The captured and stored data from the EMG electrodes 510 can then be processed by a trained machine learning technique to estimate one or more speech features, such as after filtering the data to remove interfering signals (e.g., eye blink signals and/or signals resulting from involuntary gestures or movements). The one or more speech features can then be further processed by one or more additional neural networks or machine learning techniques to generate an audible response or visual response.

The EMG communication device 119 can also include or be associated with one or more speakers (not shown). The one or more speakers can be used to audibly output the audible response estimated and generated from the subthreshold muscle activation signals detected and captured by the EMG electrodes 510. Based on the user hearing the audible response from the one or more speakers, the user can mentally adjust future inner speech generation to more accurately control the output of the EMG communication device 119.

The one or more communication devices 514 can include a Bluetooth low energy (BLE) communication interface. Such BLE communication interface enables the EMG communication device 119 to communicate wirelessly with the client device 102. Other forms of wireless communication can also be employed instead of, or in addition to, the BLE communication interface, such as a WiFi direct interface. The BLE communication interface implements a standard number of BLE communication protocols.

A first of the communications protocols implemented by the BLE interface of the EMG communication device 119 enables an unencrypted link to be established between the EMG communication device 119 and the client device 102. In this first protocol, the link-layer communication (the physical interface or medium) between the EMG communication device 119 and the client device 102 includes unencrypted data. In this first protocol, the application layer (the communication layer operating on the physically exchanged data) encrypts and decrypts data that is physically exchanged in unencrypted form over the link layer of the BLE communication interface. In this way, data exchanged over the physical layer can freely be read by an eavesdropping device, but the eavesdropping device will not be able to decipher the data that is exchanged without performing a decryption operation in the application layer.

A second of the communications protocols implemented by the BLE interface of the EMG communication device 119 enables an encrypted link to be established between the EMG communication device 119 and the client device 102. In this second protocol, the link-layer communication (the physical interface) between the EMG communication device 119 and the client device 102 receives data from the application layer and adds a first type of encryption to the data before exchanging the data over the physical medium. In this second protocol, the application layer (the communication layer operating on the physically exchanged data) may or may not use a second type of encryption to encrypt and decrypt data that is physically exchanged in encrypted form, using the first type of encryption, over the link layer of the BLE communication interface. Namely, data can be first encrypted by the application layer and then be further encrypted by the physical layer before being exchanged over the physical medium. Following the exchange over the physical medium, the data is then decrypted by the physical layer and then decrypted again (e.g., using a different type of encryption) by the application layer. In this way, data exchanged over the physical layer cannot be read by an eavesdropping device as the data is encrypted in the physical medium.

In some examples, the client device 102 communicates with the EMG communication device 119 using the first protocol to exchange raw EMG signals and uses the second protocol to exchange speech features estimated from the raw (or filtered) EMG signals between the messaging client 104 and the EMG communication device 119.

Figure 6:
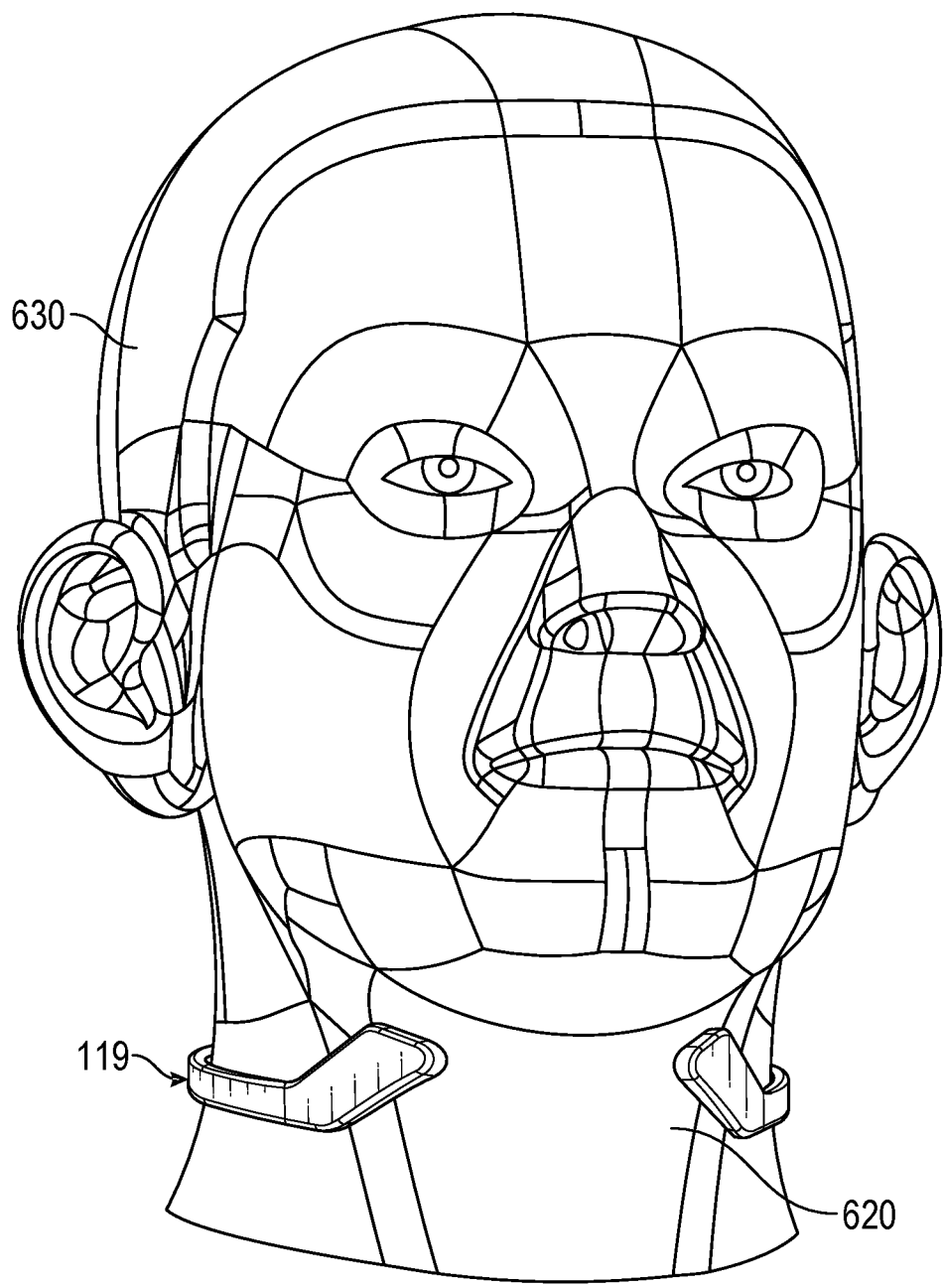

FIG. 6 is a diagrammatic representation of a user 630 wearing the EMG communication device 119, in accordance with some examples. As shown, the EMG communication device 119 is placed behind a neck 620 of the user 630. The EMG communication device 119 can completely encircle the neck 620 or partially encircle the neck 620 of the user 630.

EMG Speech Detection System

Figure 7:
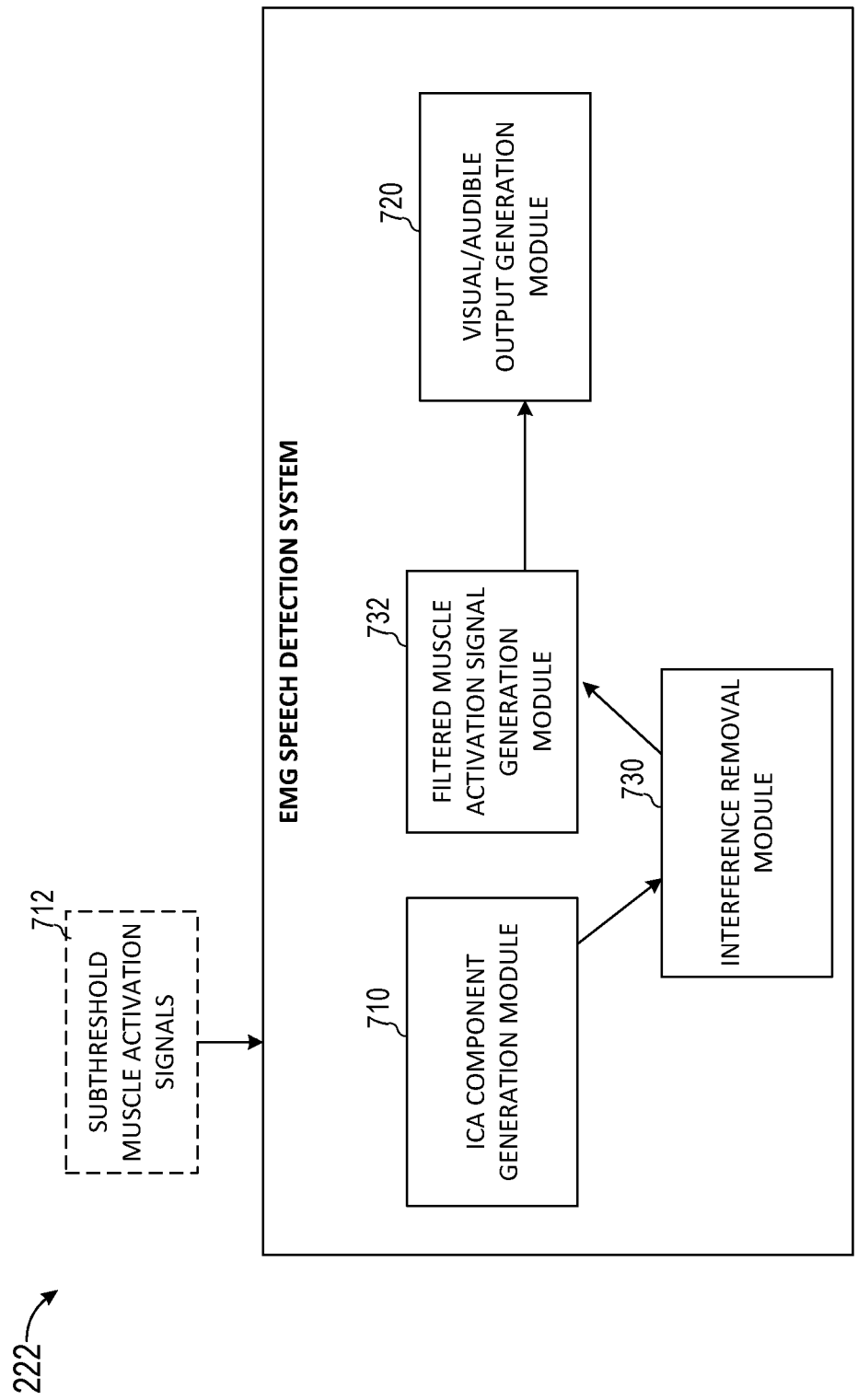
FIG. 7 is a diagrammatic representation of an EMG speech detection system, in accordance with some examples.

FIG. 7 is a diagrammatic representation of components of the EMG speech detection system 222, in accordance with some examples. The EMG speech detection system 222 includes an ICA component generation module 710, an interference removal module 730, a filtered muscle activation signal generation module 732, and a visual/audible output generation module 720.

In some examples, the ICA component generation module 710 receives an input that includes subthreshold muscle activation signals 712 from the EMG electrodes 510 of the EMG communication device 119. The subthreshold muscle activation signals 712 can be preprocessed using a low-pass or high-pass filter or any other denoising filter or technique. In some examples, the ICA component generation module 710 can implement a transform that transforms a plurality of subthreshold muscle activation signals into a plurality of maximally independent components. In some examples, the ICA component generation module 710 implements an ICA transform but any other suitable transform can be used.

The ICA component generation module 710 can generate a quantity of the plurality of maximally independent components that corresponds to a quantity of the plurality of EMG electrodes. For example, the EMG communication device 119 can include eight electrodes and, in such cases, the ICA component generation module 710 generates eight ICA components. In some examples, in the process of transforming the subthreshold muscle activation signals 712 into components, the ICA component generation module 710 can determine that the transform fails to converge. In such cases, the ICA component generation module 710 can reduce a quantity of the plurality of maximally independent components. Namely, the reduced quantity of the plurality of maximally independent components can be less than a quantity of the plurality of EMG electrodes. For example, in cases in which the transform fails to converge, the ICA component generation module 710 can generate seven or less ICA components based on signals received from eight electrodes of the EMG communication device 119.

In some examples, to improve the convergence of the ICA component generation, the ICA component generation module 710 can implement a filtering operation. For example, the ICA component generation module 710 can compute a spatial correlation matrix for the subthreshold muscle activation signals 712. The ICA component generation module 710 applies eigenvalue decomposition (EVD) to the spatial correlation matrix. The ICA component generation module 710 identifies one or more eigenvalues from the eigenvalue decomposition that fail to transgress a threshold. Namely, the ICA component generation module 710 can search EVD to find one or more eigenvalues that are relatively small in values (e.g., smaller than the threshold value). The ICA component generation module 710 can discard the one or more eigenvalues from the eigenvalue decomposition and reduce a dimension of the subthreshold muscle activation signals 712 in response. Then, the ICA component generation module 710 can apply the transform to the reduced dimension subthreshold muscle activation signals 712 to generate the ICA components.

The ICA component generation module 710 can provide the generated transform (e.g., the ICA components derived from the subthreshold muscle activation signals 712) to the interference removal module 730. The interference removal module 730 can process the ICA components received from the ICA component generation module 710 to remove one or more components that correspond to interfering signals. For example, the interference removal module 730 can remove one or more ICA components that are correlated to eye blink components.

In some examples, the interference removal module 730 can obtain an interference template that includes one or more interference components. Namely, the interference template can include an eye blink component representation. The interference removal module 730 can compute a plurality of cross correlation values between each of the plurality of maximally independent components and the one or more interference components (e.g., the eye blink component). The cross correlation values represent how similar each of the plurality of maximally independent components (e.g., the ICA components) is to the one or more interference components. The interference removal module 730 can compare the cross correlation values to each other to select a given ICA component that is associated with a highest cross correlation value. The interference removal module 730 can compare each of the cross correlation values to a threshold to determine that the cross correlation value associated with a given maximally independent component transgresses the threshold. In response, the interference removal module 730 selects the given maximally independent component from the plurality of maximally independent components for removal or filtering. The interference removal module 730 can then set the selected given maximally independent component to a zero value or some other low value. The interference removal module 730 can provide the filtered ICA components to the filtered muscle activation signal generation module 732. The filtered muscle activation signal generation module 732 can apply an inverse transform (e.g., an inverse ICA transform) to the filtered ICA components to regenerate a filtered version of the subthreshold muscle activation signals.

In some examples, the interference removal module 730 can condition or selectively filter or remove the given ICA component that is correlated highly or above a threshold to the interference component. The condition can be based on a significance value of the given maximally independent component relative to significance values of the plurality of maximally independent components. Each significance value can represent a relative presence (e.g., in the form of a percentage) of the associated maximally independent component in the subthreshold muscle activation signals 712. For example, as part of generating the ICA components, the ICA component generation module 710 can generate significance value that represents a percentage or amount which the corresponding ICA component affects or is present in the underlying subthreshold muscle activation signals 712. The significance of each ICA component can be generated by accessing a matrix of the ICA coefficients and averaging the absolute values over the electrodes followed by a normalizing operation. The matrix can be composed of ICA coefficients, such as projection strengths of the ICA components on the electrodes.

The interference removal module 730 can access a significance threshold and can determine that the significance value associated with the given maximally independent component (which has been found to be correlated beyond a threshold to an interference component) transgresses the significance threshold. In such cases, the interference removal module 730 can filter the given ICA component from the plurality of ICA components.

In some examples, the one or more interference components can be predetermined and stored in a memory of the interference removal module 730. In some examples, the one or more interference components can be generated as user specific one or more interference components to represent the particular signals that result from involuntary movements (e.g., eye blinks) of the particular user. In such cases, the interference removal module 730 can implement a machine learning model to generate the one or more interference components for a specific user to filter the interfering signals from ICA components generated from a received set of subthreshold muscle activation signals 712.

For example, the interference removal module 730 can implement a machine learning technique (e.g., a machine learning model, such as a neural network) that is trained to establish a relationship between a plurality of training subthreshold muscle activation signals and ground truth eye blink components. The neural network can include a deep neural network (DNN), such as a convolutional, recurrent, bidirectional LSTM, attention or other layers, an autoencoder/transducer or other network that can convert a subthreshold muscle activation signal to an eye blink component.

During training, the machine learning model of the interference removal module 730 can receive a given training data pair (e.g., a set of training subthreshold muscle activation signals and corresponding ground truth interference components (e.g., eye blink components, such as eye blink ICA components)) from training data stored in data structures 300. The machine learning model applies one or more machine learning techniques to the set of training subthreshold muscle activation signals. The machine learning model extracts one or more features from the set of training subthreshold muscle activation signals (or processes the raw data) to estimate an interference component, such as an estimated eye blink ICA component corresponding to the set of training subthreshold muscle activation signals.

The machine learning model of the interference removal module 730 obtains a known or predetermined ground-truth interference components associated with the set of training subthreshold muscle activation signals from the training data. The machine learning model of the interference removal module 730 compares the estimated interference components with the ground truth interference components. Based on a difference threshold of the comparison, the machine learning model of the interference removal module 730 updates one or more coefficients or parameters of the machine learning technique and obtains another set of training data that includes another set of training subthreshold muscle activation signals and corresponding ground truth interference components.

After a specified number of epochs or batches of training data have been processed and/or when a difference threshold (e.g., computed as a function of a difference between the estimated interference components and the ground-truth interference components) reaches a specified value, the machine learning model completes training, and the parameters and coefficients of the machine learning model are stored as a trained machine learning technique.

In some examples, after training, the machine learning model of the interference removal module 730 receives an input that includes subthreshold muscle activation signals 712 from the EMG electrodes 510 of the EMG communication device 119. The subthreshold muscle activation signals 712 can be preprocessed using a low-pass or high-pass filter or any other denoising filter or technique. The machine learning model of the interference removal module 730 is applied to the subthreshold muscle activation signals 712 to estimate or predict the interference component (e.g., representing an eye blink ICA component). The predicted or estimated interference component can be used to filter out or remove ICA components that are correlated with the estimated interference component from the generated ICA components of the subthreshold muscle activation signals 712. The filtered ICA components is used by the filtered muscle activation signal generation module 732 to generate a filtered version of the subthreshold muscle activation signals.

In some examples, visual/audible output generation module 720 implements a machine learning model, such as a neural network. The neural network can include a deep neural network, such as a WaveNet neural network, that is configured to transform one or more speech features derived from the filtered version of the subthreshold muscle activation signals into synthesized sound. The synthesized sound can be used as the audible representation of the one or more speech features. In some examples, the synthesized sound is communicated to another component, such as to the client device 102 and/or to a messaging client 104. In some examples, the synthesized sound is output through one or more speakers for a user to hear. Namely, a user can perform inner speech (or imaginary speech) and can then receive feedback in the form of the synthesized sound to verify that the inner speech was accurately processed to generate the synthesized sound. In some examples, the synthesized sound is output to an AR/VR application to control operations of the AR/VR application. In another example, the synthesized sound can be transmitted as a voice or audible message to another user via the messaging client 104.

In some examples, one or more speech features derived from the filtered version of the subthreshold muscle activation signals are processed by a DNN classifier, such as VGGish, YamNet or other suitable classifier, to classify which word was covertly spoken out of a predefined list of words or phonemes. Namely, the speech features can be processed by the DNN classifier to estimate one or more textual words or phrases associated with the one or more speech features. The textual words or phrases can be used as the visual representation of the one or more speech features. In some examples, the textual words or phrases are communicated to another component, such as to the client device 102 and/or to a messaging client 104. In some examples, the textual words or phrases are presented on a graphical user interface for a user to review. Namely, a user can perform inner speech and can then receive feedback in the form of the visual textual words or phrases to verify that the inner speech was accurately processed to generate the textual words or phrases. In another example, the textual words or phrases are output to an AR/VR application to control operations of the AR/VR application. In another example, the textual words or phrases can be transmitted as a textual message to another user via the messaging client 104.

In some examples, the DNN classifier fails to identify any words or phrases associated with the one or more speech features. In such cases, the visual/audible output generation module 720 can inform the user that inner speech failed to be detected and can request or instruct the user to repeat or reperform the inner speech.

Figure 8A:
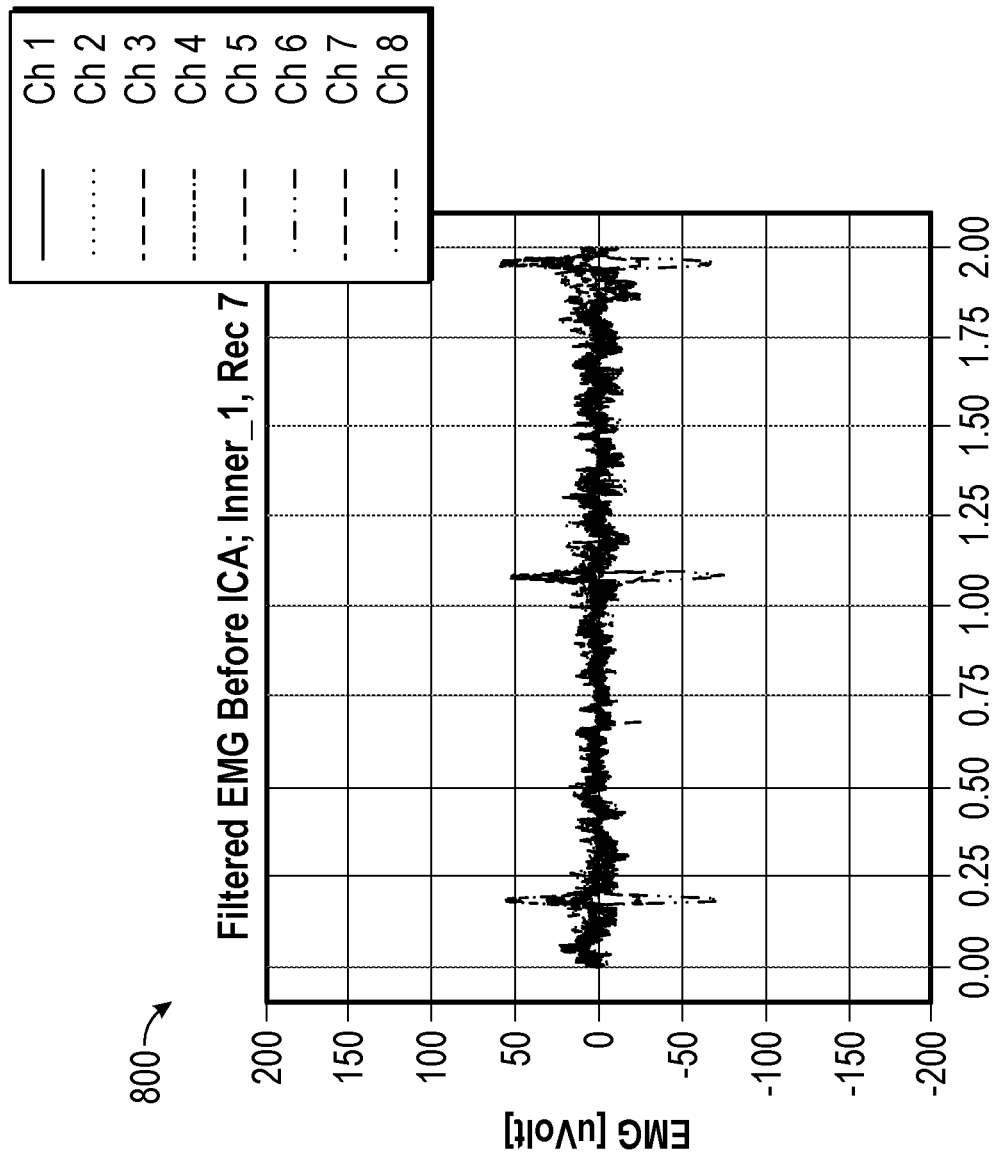
FIGS. 8A-D are illustrative outputs of the EMG speech detection system, in accordance with some examples.
Figure 8B:
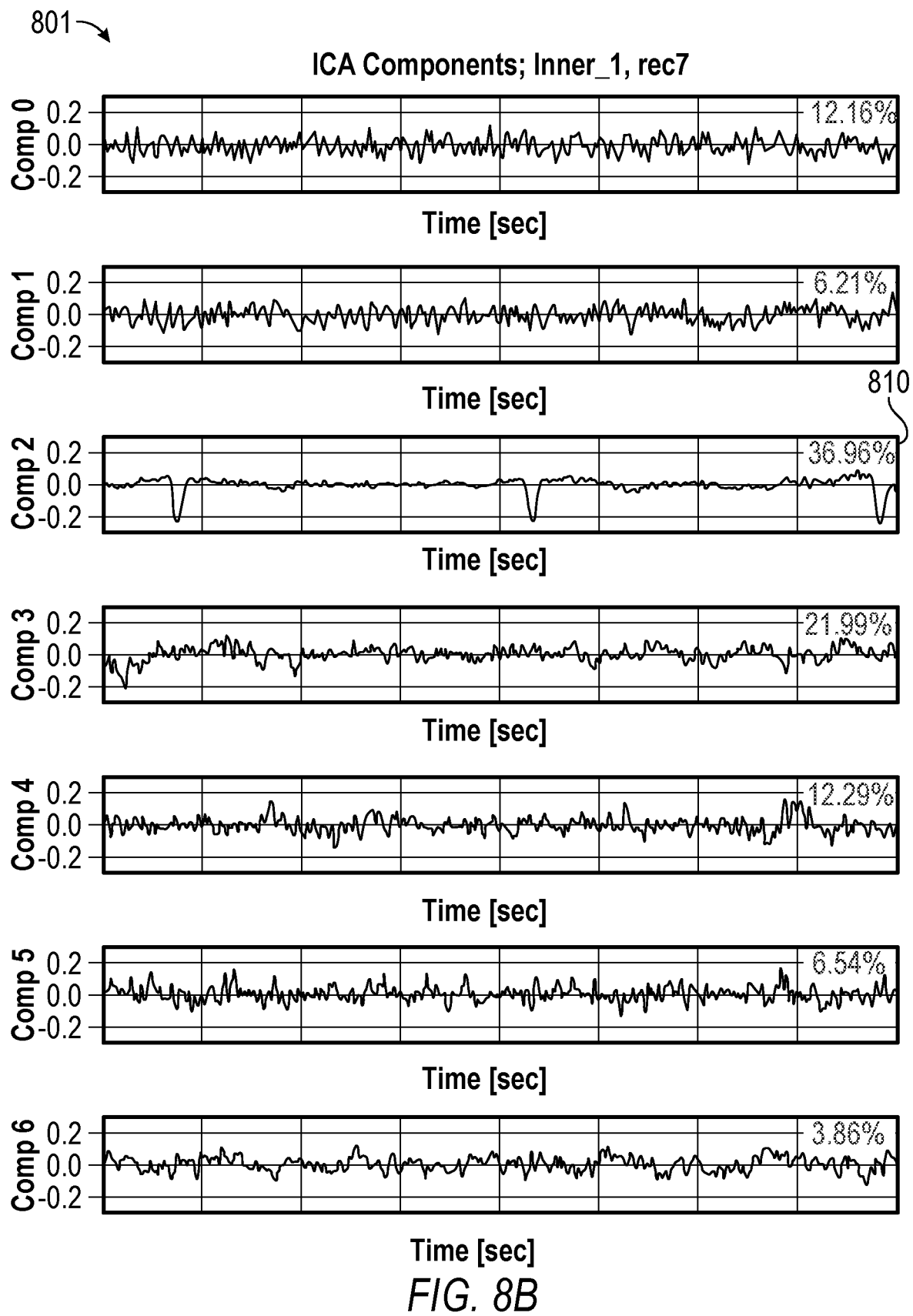
Figure 8C:
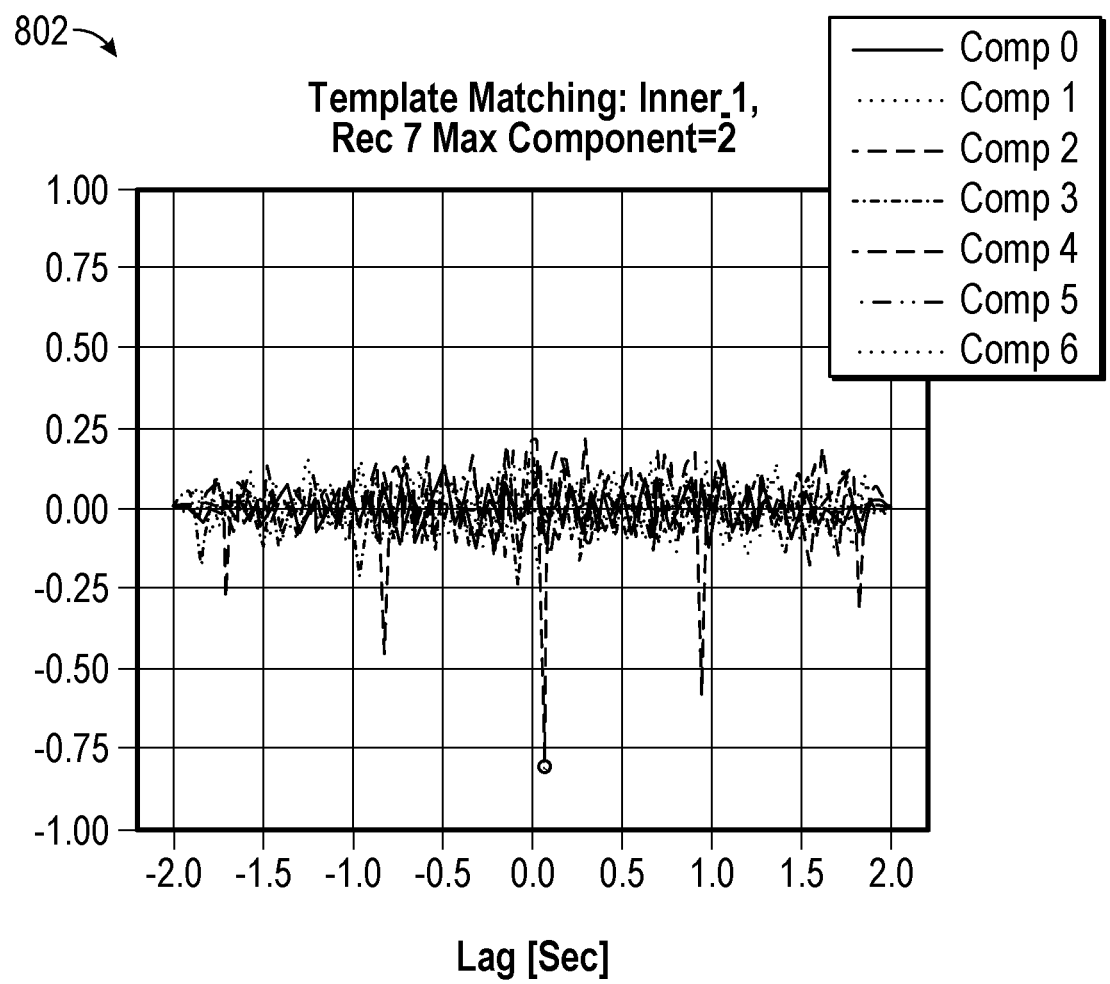

FIG. 8A is an illustrative output of the EMG speech detection system 222, in accordance with some examples. As shown in FIG. 8A, subthreshold muscle activation signals 712 can be received and presented in a plot or graph 800. The subthreshold muscle activation signals 712 can be color coded in the plot or graph 800 to represent each EMG electrode from which the corresponding subthreshold muscle activation signals 712 was received. The subthreshold muscle activation signals 712 can be processed by the ICA component generation module 710. The ICA component generation module 710 can generate a set of ICA components shown by respective plots or graphs 801 (FIG. 8B) by applying an ICA or other transform to the subthreshold muscle activation signals 712. The interference removal module 730 can compute cross correlation values between the set of ICA components and generate the cross-correlation values shown by the plot or graph 802 (FIG. 8C) and one or more interference components (e.g., an eye blink component, such as one derived from an eye blink template). The interference removal module 730 can determine that a particular ICA component 810 (FIG. 8B) is associated with a cross correlation value that is greater than all of the other cross correlation values and transgresses or exceeds a specified threshold value.

Figure 8D:
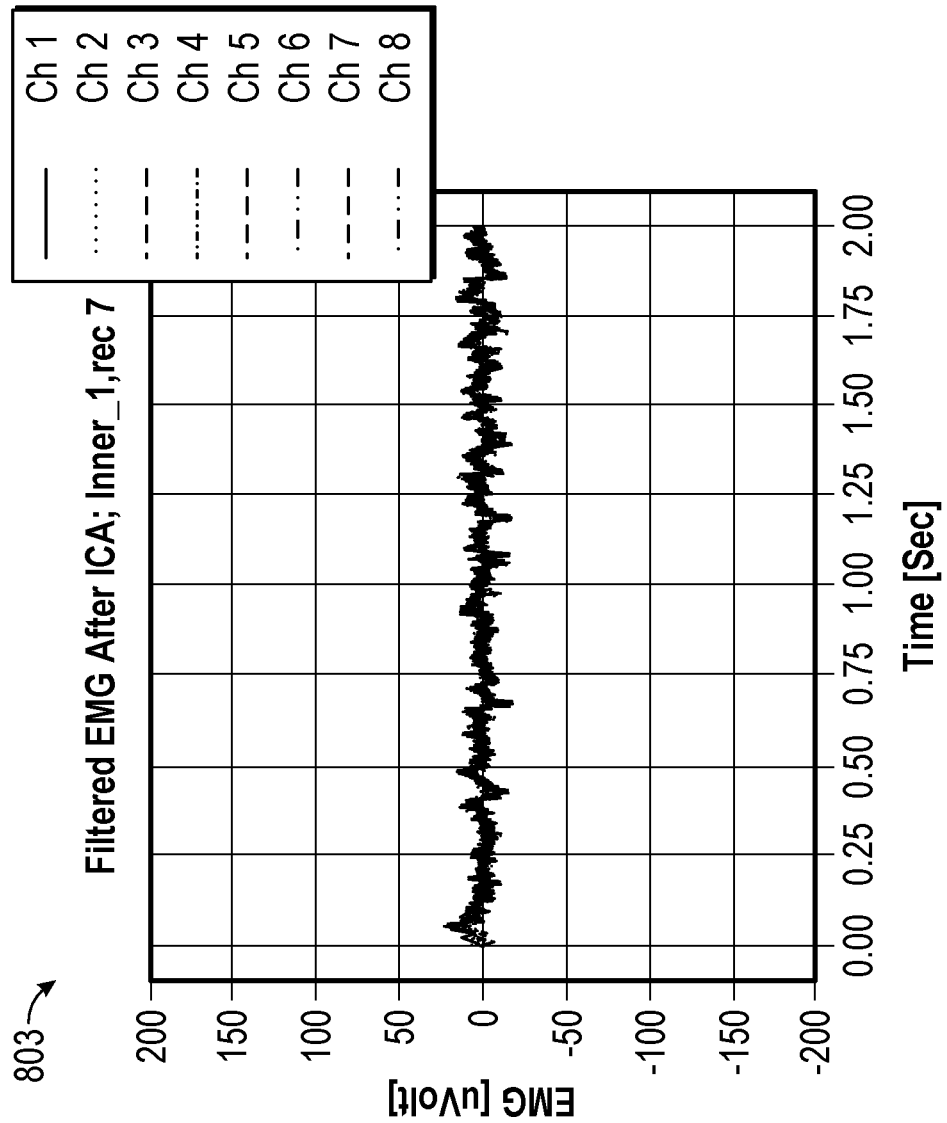

In such cases, the interference removal module 730 can set the particular ICA component 810 to a zero value or negligible value to generate a filtered set of ICA components. The interference removal module 730 can then provide the filtered set of ICA components to the filtered muscle activation signal generation module 732. The filtered muscle activation signal generation module 732 can apply an inverse transform or inverse ICA transform to the filtered set of ICA components. In response, the filtered muscle activation signal generation module 732 generates a filtered version of the subthreshold muscle activation signals represented by plot or graph 803 (FIG. 8D).

Figure 9:
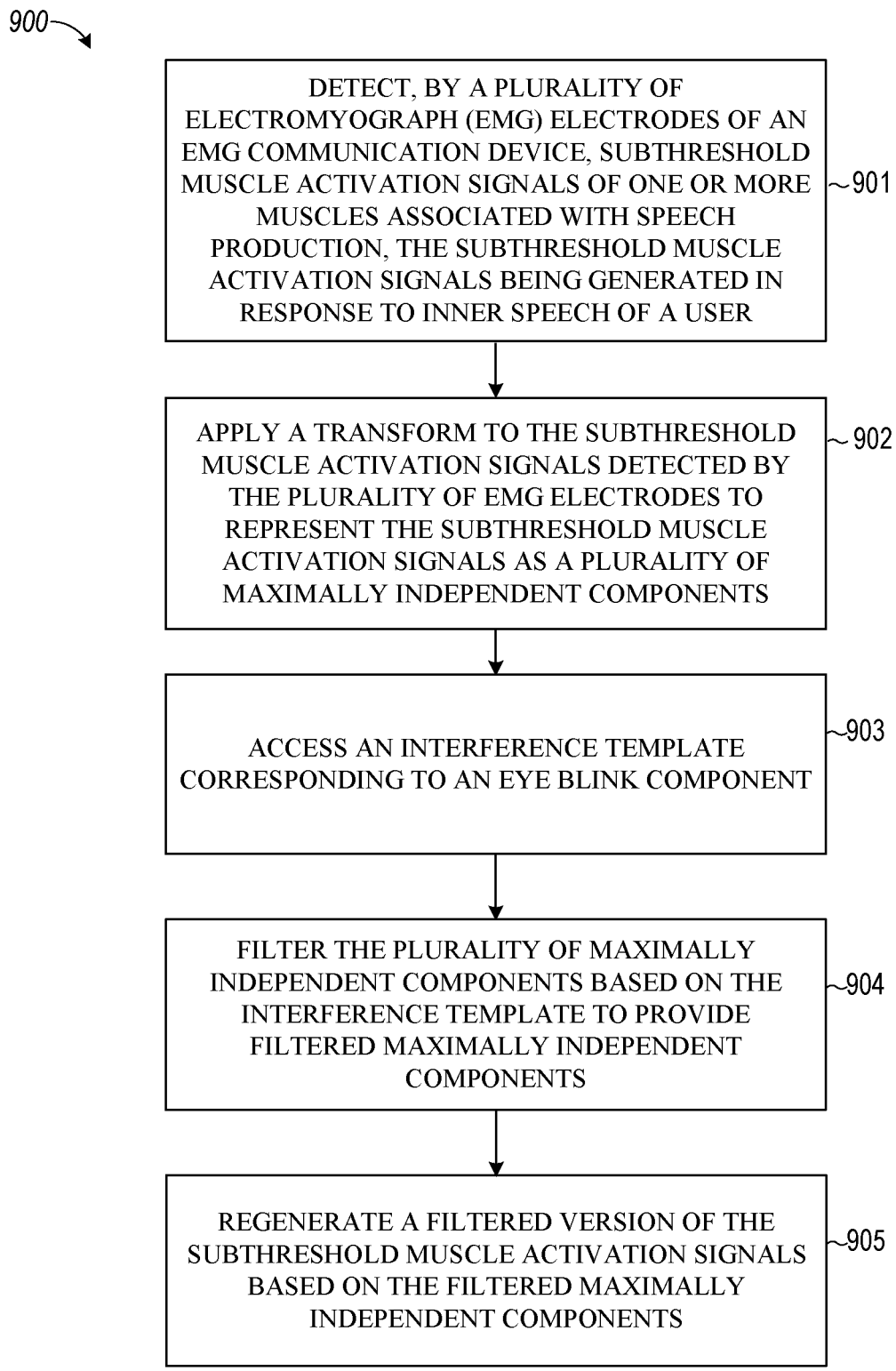
FIG. 9 is a flowchart showing example operations of the EMG speech detection system, in accordance with some examples.

FIG. 9 is a flowchart illustrating example operations of the EMG speech detection system 222 in performing a process 900, according to some examples. The process 900 may be embodied in computer-readable instructions for execution by one or more processors such that the operations of the process 900 may be performed in part or in whole by the functional components of the EMG speech detection system 222; accordingly, the process 900 is described below by way of example with reference thereto. However, in other examples, at least some of the operations of the process 900 may be deployed on various other hardware configurations. The process 900 is therefore not intended to be limited to the EMG speech detection system 222 and can be implemented in whole, or in part, by any other component. Some or all of the operations of process 900 can be in parallel, out of order, or entirely omitted.

At operation 901, the EMG speech detection system 222 detects, by a plurality of electromyograph EMG electrodes of an EMG communication device, subthreshold muscle activation signals of one or more muscles associated with speech production, the subthreshold muscle activation signals being generated in response to inner speech of a user, as discussed above.

At operation 902, the EMG speech detection system 222 applies a transform (e.g., an ICA transform) to the subthreshold muscle activation signals detected by the plurality of EMG electrodes to represent the subthreshold muscle activation signals as a plurality of maximally independent components, as discussed above.

At operation 903, the EMG speech detection system 222 accesses an interference template corresponding to an eye blink component, as discussed above.

At operation 904, the EMG speech detection system 222 filters the plurality of maximally independent components based on the interference template to provide filtered maximally independent components, as discussed above.

At operation 905, the EMG speech detection system 222 regenerates a filtered version of the subthreshold muscle activation signals based on the filtered maximally independent components, as discussed above. For example, the EMG speech detection system 222 can apply an inverse transform (e.g., an inverse ICA transform) to the filtered maximally independent components to generate the filtered version of the subthreshold muscle activation signals.

Machine Architecture

Figure 10:
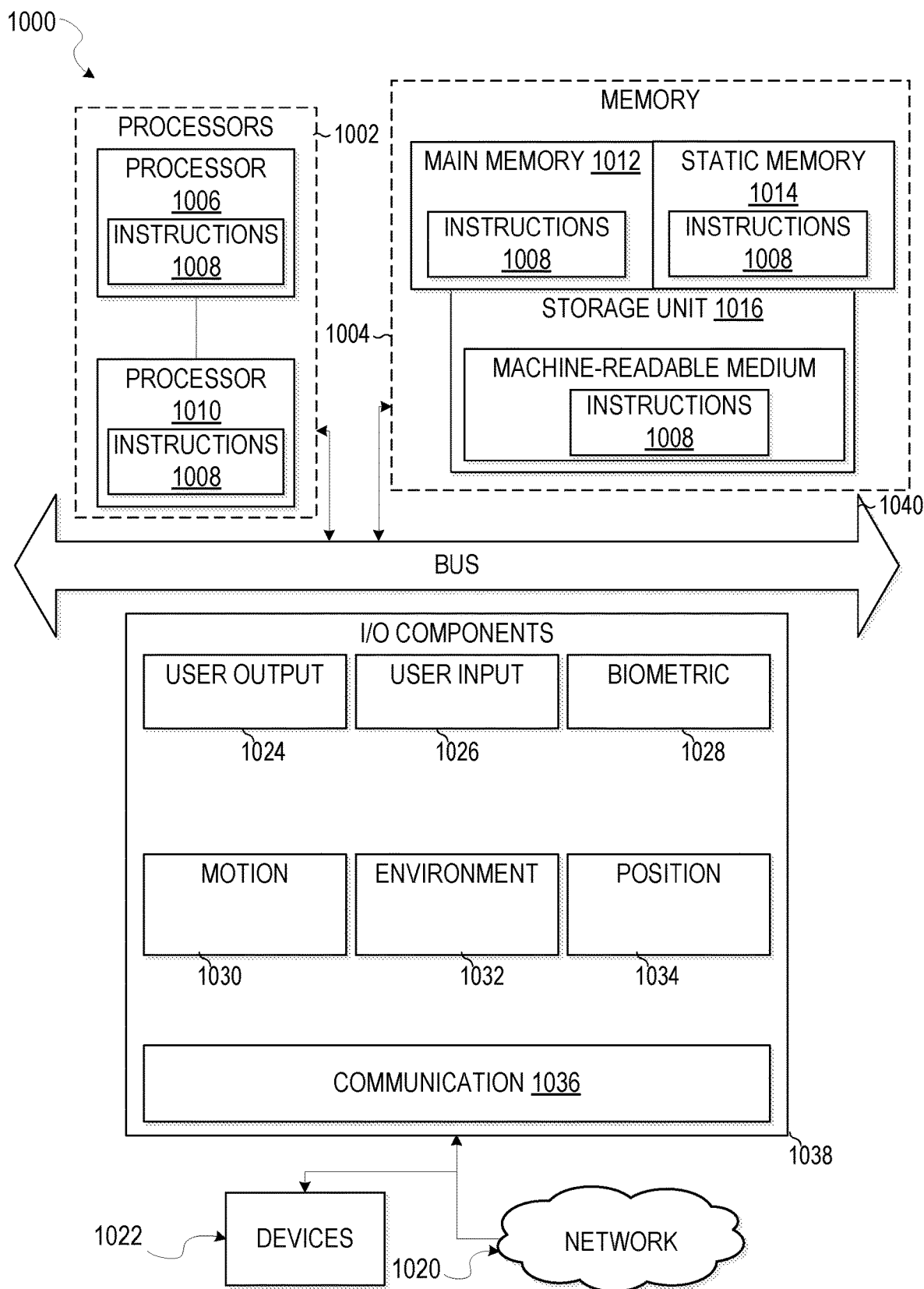
FIG. 10 is a diagrammatic representation of a machine in the form of a computer system within which a set of instructions may be executed for causing the machine to perform any one or more of the methodologies discussed herein, in accordance with some examples.

FIG. 10 is a diagrammatic representation of a machine 1000 within which instructions 1008 (e.g., software, a program, an application, an applet, an app, or other executable code) for causing the machine 1000 to perform any one or more of the methodologies discussed herein may be executed. For example, the instructions 1008 may cause the machine 1000 to execute any one or more of the methods described herein. The instructions 1008 transform the general, non-programmed machine 1000 into a particular machine 1000 programmed to carry out the described and illustrated functions in the manner described. The machine 1000 may operate as a standalone device or may be coupled (e.g., networked) to other machines. In a networked deployment, the machine 1000 may operate in the capacity of a server machine or a client machine in a server-client network environment, or as a peer machine in a peer-to-peer (or distributed) network environment. The machine 1000 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smartphone, a mobile device, a wearable device (e.g., a smartwatch), a smart home device (e.g., a smart appliance), other smart devices, a web appliance, a network router, a network switch, a network bridge, or any machine capable of executing the instructions 1008, sequentially or otherwise, that specify actions to be taken by the machine 1000. Further, while only a single machine 1000 is illustrated, the term "machine" shall also be taken to include a collection of machines that individually or jointly execute the instructions 1008 to perform any one or more of the methodologies discussed herein. The machine 1000, for example, may comprise the client device 102 or any one of a number of server devices forming part of the messaging server system 108. In some examples, the machine 1000 may also comprise both client and server systems, with certain operations of a particular method or algorithm being performed on the server-side and with certain operations of the particular method or algorithm being performed on the client-side.

The machine 1000 may include processors 1002, memory 1004, and input/output (I/O) components 1038, which may be configured to communicate with each other via a bus 1040. In an example, the processors 1002 (e.g., a Central Processing Unit (CPU), a Reduced Instruction Set Computing (RISC) Processor, a Complex Instruction Set Computing (CISC) Processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, a processor 1006 and a processor 1010 that execute the instructions 1008. The term "processor" is intended to include multi-core processors that may comprise two or more independent processors (sometimes referred to as "cores") that may execute instructions contemporaneously. Although FIG. 10 shows multiple processors 1002, the machine 1000 may include a single processor with a single-core, a single processor with multiple cores (e.g., a multi-core processor), multiple processors with a single core, multiple processors with multiples cores, or any combination thereof.

The memory 1004 includes a main memory 1012, a static memory 1014, and a storage unit 1016, all accessible to the processors 1002 via the bus 1040. The main memory 1004, the static memory 1014, and the storage unit 1016 store the instructions 1008 embodying any one or more of the methodologies or functions described herein. The instructions 1008 may also reside, completely or partially, within the main memory 1012, within the static memory 1014, within machine-readable medium 1018 within the storage unit 1016, within at least one of the processors 1002 (e.g., within the processor's cache memory), or any suitable combination thereof, during execution thereof by the machine 1000.

The I/O components 1038 may include a wide variety of components to receive input, provide output, produce output, transmit information, exchange information, capture measurements, and so on. The specific I/O components 1038 that are included in a particular machine will depend on the type of machine. For example, portable machines such as mobile phones may include a touch input device or other such input mechanisms, while a headless server machine will likely not include such a touch input device. It will be appreciated that the I/O components 1038 may include many other components that are not shown in FIG. 10. In various examples, the I/O components 1038 may include user output components 1024 and user input components 1026. The user output components 1024 may include visual components (e.g., a display such as a plasma display panel (PDP), a light-emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The user input components 1026 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and force of touches or touch gestures, or other tactile input components), audio input components (e.g., a microphone), and the like.

In further examples, the I/O components 1038 may include biometric components 1028, motion components 1030, environmental components 1032, or position components 1034, among a wide array of other components. For example, the biometric components 1028 include components to detect expressions (e.g., hand expressions, facial expressions, vocal expressions, body gestures, or eye-tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 1030 include acceleration sensor components (e.g., accelerometer), gravitation sensor components, rotation sensor components (e.g., gyroscope).

The environmental components 1032 include, for example, one or cameras (with still image/photograph and video capabilities), illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment.

With respect to cameras, the client device 102 may have a camera system comprising, for example, front cameras on a front surface of the client device 102 and rear cameras on a rear surface of the client device 102. The front cameras may, for example, be used to capture still images and video of a user of the client device 102 (e.g., "selfies"), which may then be augmented with augmentation data (e.g., filters) described above. The rear cameras may, for example, be used to capture still images and videos in a more traditional camera mode, with these images similarly being augmented with augmentation data. In addition to front and rear cameras, the client device 102 may also include a 360° camera for capturing 360° photographs and videos.

Further, the camera system of a client device 102 may include dual rear cameras (e.g., a primary camera as well as a depth-sensing camera), or even triple, quad or penta rear camera configurations on the front and rear sides of the client device 102. These multiple cameras systems may include a wide camera, an ultra-wide camera, a telephoto camera, a macro camera, and a depth sensor, for example.

The position components 1034 include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1038 further include communication components 1036 operable to couple the machine 1000 to a network 1020 or devices 1022 via respective coupling or connections. For example, the communication components 1036 may include a network interface component or another suitable device to interface with the network 1020. In further examples, the communication components 1036 may include wired communication components, wireless communication components, cellular communication components, Near Field Communication (NFC) components, Bluetooth® components (e.g., Bluetooth® Low Energy), WiFi® components, and other communication components to provide communication via other modalities. The devices 1022 may be another machine or any of a wide variety of peripheral devices (e.g., a peripheral device coupled via a USB).

Moreover, the communication components 1036 may detect identifiers or include components operable to detect identifiers. For example, the communication components 1036 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1036, such as location via Internet Protocol (IP) geolocation, location via Wi-Fi® signal triangulation, location via detecting an NFC beacon signal that may indicate a particular location, and so forth.

The various memories (e.g., main memory 1012, static memory 1014, and memory of the processors 1002) and storage unit 1016 may store one or more sets of instructions and data structures (e.g., software) embodying or used by any one or more of the methodologies or functions described herein. These instructions (e.g., the instructions 1008), when executed by processors 1002, cause various operations to implement the disclosed examples.

The instructions 1008 may be transmitted or received over the network 1020, using a transmission medium, via a network interface device (e.g., a network interface component included in the communication components 1036) and using any one of several well-known transfer protocols (e.g., hypertext transfer protocol (HTTP)). Similarly, the instructions 1008 may be transmitted or received using a transmission medium via a coupling (e.g., a peer-to-peer coupling) to the devices 1022.

Software Architecture

Figure 11:
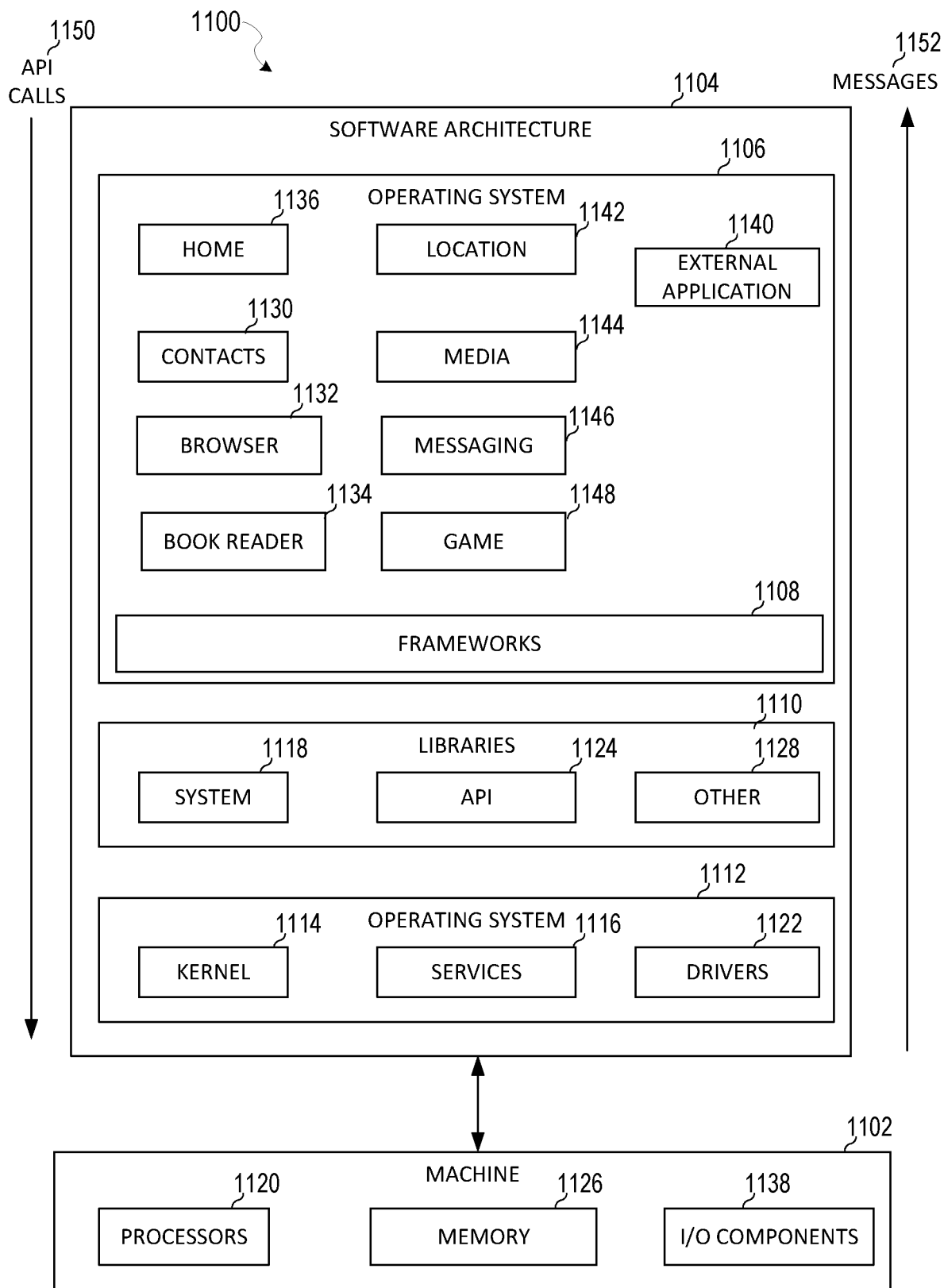
FIG. 11 is a block diagram showing a software architecture within which examples may be implemented.

FIG. 11 is a block diagram 1100 illustrating a software architecture 1104, which can be installed on any one or more of the devices described herein. The software architecture 1104 is supported by hardware such as a machine 1102 that includes processors 1120, memory 1126, and I/O components 1138. In this example, the software architecture 1104 can be conceptualized as a stack of layers, where each layer provides a particular functionality. The software architecture 1104 includes layers such as an operating system 1112, libraries 1110, frameworks 1108, and applications 1106. Operationally, the applications 1106 invoke API calls 1150 through the software stack and receive messages 1152 in response to the API calls 1150.

The operating system 1112 manages hardware resources and provides common services. The operating system 1112 includes, for example, a kernel 1114, services 1116, and drivers 1122. The kernel 1114 acts as an abstraction layer between the hardware and the other software layers. For example, the kernel 1114 provides memory management, processor management (e.g., scheduling), component management, networking, and security settings, among other functionality. The services 1116 can provide other common services for the other software layers. The drivers 1122 are responsible for controlling or interfacing with the underlying hardware. For instance, the drivers 1122 can include display drivers, camera drivers, BLUETOOTH® or BLUETOOTH® Low Energy drivers, flash memory drivers, serial communication drivers (e.g., USB drivers), WI-FI® drivers, audio drivers, power management drivers, and so forth.

The libraries 1110 provide a common low-level infrastructure used by the applications 1106. The libraries 1110 can include system libraries 1118 (e.g., C standard library) that provide functions such as memory allocation functions, string manipulation functions, mathematic functions, and the like. In addition, the libraries 1110 can include API libraries 1124 such as media libraries (e.g., libraries to support presentation and manipulation of various media formats such as Moving Picture Experts Group-4 (MPEG4), Advanced Video Coding (H.264 or AVC), Moving Picture Experts Group Layer-3 (MP3), Advanced Audio Coding (AAC), Adaptive Multi-Rate (AMR) audio codec, Joint Photographic Experts Group (JPEG or JPG), or Portable Network Graphics (PNG)), graphics libraries (e.g., an OpenGL framework used to render in two dimensions (2D) and three dimensions (3D) in a graphic content on a display), database libraries (e.g., SQLite to provide various relational database functions), web libraries (e.g., WebKit to provide web browsing functionality), and the like. The libraries 1110 can also include a wide variety of other libraries 1128 to provide many other APIs to the applications 1106.

The frameworks 1108 provide a common high-level infrastructure that is used by the applications 1106. For example, the frameworks 1108 provide various graphical user interface (GUI) functions, high-level resource management, and high-level location services. The frameworks 1108 can provide a broad spectrum of other APIs that can be used by the applications 1106, some of which may be specific to a particular operating system or platform.

In an example, the applications 1106 may include a home application 1136, a contacts application 1130, a browser application 1132, a book reader application 1134, a location application 1142, a media application 1144, a messaging application 1146, a game application 1148, and a broad assortment of other applications such as an external application 1140. The applications 1106 are programs that execute functions defined in the programs. Various programming languages can be employed to create one or more of the applications 1106, structured in a variety of manners, such as object-oriented programming languages (e.g., Objective-C, Java, or C++) or procedural programming languages (e.g., C or assembly language). In a specific example, the external application 1140 (e.g., an application developed using the ANDROID™ or IOS™ software development kit (SDK) by an entity other than the vendor of the particular platform) may be mobile software running on a mobile operating system such as IOS™, ANDROID™ WINDOWS® Phone, or another mobile operating system. In this example, the external application 1140 can invoke the API calls 1150 provided by the operating system 1112 to facilitate functionality described herein Glossary "CARRIER SIGNAL" in this context refers to any intangible medium that is capable of storing, encoding, or carrying transitory or non-transitory instructions for execution by the machine, and includes digital or analog communications signals or other intangible medium to facilitate communication of such instructions. Instructions may be transmitted or received over the network using a transitory or non-transitory transmission medium via a network interface device and using any one of a number of well-known transfer protocols.

"CLIENT DEVICE" in this context refers to any machine that interfaces to a communications network to obtain resources from one or more server systems or other client devices. A client device may be, but is not limited to, a mobile phone, desktop computer, laptop, PDAs, smart phones, tablets, ultra books, netbooks, laptops, multi-processor systems, microprocessor-based or programmable consumer electronics, game consoles, set-top boxes, or any other communication device that a user may use to access a network.

"COMMUNICATIONS NETWORK" in this context refers to one or more portions of a network that may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

"EPHEMERAL MESSAGE" in this context refers to a message that is accessible for a time-limited duration. An ephemeral message may be a text, an image, a video, and the like. The access time for the ephemeral message may be set by the message sender. Alternatively, the access time may be a default setting or a setting specified by the recipient. Regardless of the setting technique, the message is transitory.

"MACHINE-READABLE MEDIUM" in this context refers to a component, device, or other tangible media able to store instructions and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., code) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

"COMPONENT" in this context refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various examples, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a Field-Programmable Gate Array (FPGA) or an ASIC. A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering examples in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In examples in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices, and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some examples, the processors or processor-implemented components may be located in a single geographic location (e.g., within a home environment, an office environment, or a server farm). In other examples, the processors or processor-implemented components may be distributed across a number of geographic locations.

"PROCESSOR" in this context refers to any circuit or virtual circuit (a physical circuit emulated by logic executing on an actual processor) that manipulates data values according to control signals (e.g., "commands," "op codes," "machine code,", etc.) and which produces corresponding output signals that are applied to operate a machine. A processor may, for example, be a Central Processing Unit (CPU), a Reduced Instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC) or any combination thereof. A processor may further be a multi-core processor having two or more independent processors (sometimes referred to as "cores") that may execute instructions contemporaneously.

"TIMESTAMP" in this context refers to a sequence of characters or encoded information identifying when a certain event occurred, for example giving date and time of day, sometimes accurate to a small fraction of a second.

Changes and modifications may be made to the disclosed examples without departing from the scope of the present disclosure. These and other changes or modifications are intended to be included within the scope of the present disclosure, as expressed in the following claims.

Modules, Components, and Logic

Certain examples are described herein as including logic or a number of components, modules, or mechanisms. Modules can constitute either software modules (e.g., code embodied on a machine-readable medium or in a transmission signal) or hardware modules. A "hardware module" is a tangible unit capable of performing certain operations and can be configured or arranged in a certain physical manner. In various examples, one or more computer systems (e.g., a standalone computer system, a client computer system, or a server computer system) or one or more hardware modules of a computer system (e.g., a processor or group of processors) is configured by software (e.g., an application or application portion) as a hardware module that operates to perform certain operations as described herein.

In some examples, a hardware module is implemented mechanically, electronically, or any suitable combination thereof. For example, a hardware module can include dedicated circuitry or logic that is permanently configured to perform certain operations. For example, a hardware module can be a special-purpose processor, such as a Field-Programmable Gate Array (FPGA) or an Application-Specific Integrated Circuit (ASIC). A hardware module may also include programmable logic or circuitry that is temporarily configured by software to perform certain operations. For example, a hardware module can include software encompassed within a general-purpose processor or other programmable processor. It will be appreciated that the decision to implement a hardware module mechanically, in dedicated and permanently configured circuitry, or in temporarily configured circuitry (e.g., configured by software) can be driven by cost and time considerations.

Accordingly, the phrase "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering examples in which hardware modules are temporarily configured (e.g., programmed), each of the hardware modules need not be configured or instantiated at any one instance in time. For example, where a hardware module comprises a general-purpose processor configured by software to become a special-purpose processor, the general-purpose processor may be configured as respectively different special-purpose processors (e.g., comprising different hardware modules) at different times. Software can accordingly configure a particular processor or processors, for example, to constitute a particular hardware module at one instance of time and to constitute a different hardware module at a different instance of time.

Hardware modules can provide information to, and receive information from, other hardware modules. Accordingly, the described hardware modules can be regarded as being communicatively coupled. Where multiple hardware modules exist contemporaneously, communications can be achieved through signal transmission (e.g., over appropriate circuits and buses) between or among two or more of the hardware modules. In examples in which multiple hardware modules are configured or instantiated at different times, communications between or among such hardware modules may be achieved, for example, through the storage and retrieval of information in memory structures to which the multiple hardware modules have access. For example, one hardware module performs an operation and stores the output of that operation in a memory device to which it is communicatively coupled. A further hardware module can then, at a later time, access the memory device to retrieve and process the stored output. Hardware modules can also initiate communications with input or output devices, and can operate on a resource (e.g., a collection of information).

The various operations of example methods described herein can be performed, at least partially, by one or more processors that are temporarily configured (e.g., by software) or permanently configured to perform the relevant operations. Whether temporarily or permanently configured, such processors constitute processor-implemented modules that operate to perform one or more operations or functions described herein. As used herein, "processor-implemented module" refers to a hardware module implemented using one or more processors.

Similarly, the methods described herein can be at least partially processor-implemented, with a particular processor or processors being an example of hardware. For example, at least some of the operations of a method can be performed by one or more processors or processor-implemented modules. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API).

The performance of certain of the operations may be distributed among the processors, not only residing within a single machine, but deployed across a number of machines. In some examples, the processors or processor-implemented modules are located in a single geographic location (e.g., within a home environment, an office environment, or a server farm). In other examples, the processors or processor-implemented modules are distributed across a number of geographic locations.

What is claimed is:

1. A method comprising:
    detecting, by a plurality of electromyograph (EMG) electrodes of an EMG communication device, subthreshold muscle activation signals of one or more muscles associated with speech production, the subthreshold muscle activation signals being generated in response to inner speech of a user;
    applying a transform to the subthreshold muscle activation signals detected by the plurality of EMG electrodes to represent the subthreshold muscle activation signals as a plurality of maximally independent components, wherein a quantity of the plurality of maximally independent components corresponds to a quantity of the plurality of EMG electrodes;
    accessing an interference template corresponding to an eye blink component;
    filtering the plurality of maximally independent components based on the interference template to provide filtered maximally independent components; and
    regenerating a filtered version of the subthreshold muscle activation signals based on the filtered maximally independent components.

2. The method of claim 1, wherein the transform comprises an independent component analysis (ICA) transform.

3. The method of claim 1, further comprising:
    applying an inverse transform to the filtered maximally independent components to regenerate the filtered version of the subthreshold muscle activation signals.

4. The method of claim 3, wherein the inverse transform comprises an inverse independent component analysis (ICA) transform.

5. The method of claim 1, wherein filtering the plurality of maximally independent components comprises setting a given maximally independent component corresponding to the eye blink component to a zero value.

6. The method of claim 5, further comprising:
computing a plurality of cross correlation values between each of the plurality of maximally independent components and the eye blink component; and
selecting the given maximally independent component from the plurality of maximally independent components in response to determining that the given maximally independent component is associated with a greatest cross correlation value of the plurality of cross correlation values.

7. The method of claim 6, further comprising:
determining that a cross correlation value associated with the given maximally independent component transgresses a threshold, the plurality of maximally independent components being filtered in response to determining that the cross correlation value associated with the given maximally independent component transgresses the threshold.

8. The method of claim 6, further comprising:
determining a significance value of the given maximally independent component relative to significance values of the plurality of maximally independent components, each significance value representing a relative presence of the associated maximally independent component in the subthreshold muscle activation signals.

9. The method of claim 8, further comprising:
accessing a significance threshold; and
determining that the significance value associated with the given maximally independent component transgresses the significance threshold, the plurality of maximally independent components being filtered in response to determining that the significance value associated with the given maximally independent component transgresses the significance threshold.

10. The method of claim 1, further comprising:
generating at least one of a visual or audible output based on the filtered version of the subthreshold muscle activation signals; and
causing the at least one the visual or audible output to be processed by a messaging application to engage a feature of the messaging application.

11. The method of claim 1, wherein the inner speech of the user comprises imaginary speech including a voluntary act of speaking without moving any of the muscles associated with speech production.

12. The method of claim 1, wherein the EMG communication device comprises a wearable collar device, the wearable collar device comprising the one or more EMG electrodes, a microphone, and a communication device, the EMG communication device being in communication with a mobile device that implements a messaging application.

13. The method of claim 1, further comprising:
generating the interference template using a machine learning model.

14. The method of claim 13, further comprising training the machine learning model by performing operations comprising:
receiving training data comprising a training set of subthreshold muscle activation signals and a training set of ground truth eye blink components;
processing a first subthreshold muscle activation signal of the training set by the machine learning model to generate an estimated eye blink component;
computing a deviation between the estimated eye blink component and the ground truth eye blink component associated with the first subthreshold muscle activation signal;
updating one or more parameters of the machine learning model based on the computed deviation; and
repeating the operations for training for each of the training set of subthreshold muscle activation signals.

15. A system comprising:
a storage device of an electromyograph (EMG) communication device; and
at least one processor of the EMG communication device configured to perform operations comprising:
detecting, by a plurality of EMG electrodes of the EMG communication device, subthreshold muscle activation signals of one or more muscles associated with speech production, the subthreshold muscle activation signals being generated in response to inner speech of a user;
applying a transform to the subthreshold muscle activation signals detected by the plurality of EMG electrodes to represent the subthreshold muscle activation signals as a plurality of maximally independent components, wherein a quantity of the plurality of maximally independent components corresponds to a quantity of the plurality of EMG electrodes;
accessing an interference template corresponding to an eye blink component;
filtering the plurality of maximally independent components based on the interference template to provide filtered maximally independent components; and
regenerating a filtered version of the subthreshold muscle activation signals based on the filtered maximally independent components.

16. The method of claim 1, further comprising:
determining that the transform fails to converge; and
in response to determining that the transform fails to converge, reducing a quantity of the plurality of maximally independent components, wherein the reduced quantity of the plurality of maximally independent components is less than a quantity of the plurality of EMG electrodes.

17. The method of claim 16, wherein the quantity of the plurality of maximally independent components continues to be reduced until the transform successfully converges.

18. The method of claim 16, further comprising:
computing a spatial correlation matrix for the subthreshold muscle activation signals;
applying eigenvalue decomposition (EVD) to the spatial correlation matrix;
identifying one or more eigenvalues from the eigenvalue decomposition that fail to transgress a threshold;
discarding the one or more eigenvalues from the eigenvalue decomposition;
reducing a dimension of the subthreshold muscle activation signals in response to discarding the one or more eigenvalues from the eigenvalue decomposition; and
applying the transform to the subthreshold muscle activation signals having the reduced dimension.

19. The system of claim 15, the operations comprising generating the interference template using a machine learning model.

20. A non-transitory machine-readable storage medium comprising instructions that, when executed by one or more processors of a machine, cause the machine to perform operations comprising:
detecting, by a plurality of electromyograph (EMG) electrodes of an EMG communication device, subthreshold muscle activation signals of one or more muscles associated with speech production, the subthreshold muscle activation signals being generated in response to inner speech of a user;

applying a transform to the subthreshold muscle activation signals detected by the plurality of EMG electrodes to represent the subthreshold muscle activation signals as a plurality of maximally independent components, wherein a quantity of the plurality of maximally independent components corresponds to a quantity of the plurality of EMG electrodes;

accessing an interference template corresponding to an eye blink component;

filtering the plurality of maximally independent components based on the interference template to provide filtered maximally independent components; and regenerating a filtered version of the subthreshold muscle activation signals based on the filtered maximally independent components.

* * * * *